United States Patent
Hunter et al.

(10) Patent No.: US 6,333,347 B1
(45) Date of Patent: *Dec. 25, 2001

(54) INTRAPERICARDIAL DELIVERY OF ANTI-MICROTUBULE AGENTS

(75) Inventors: William L. Hunter, Vancouver (CA); Keith L. March, Indianapolis, IN (US)

(73) Assignee: Angiotech Pharmaceuticals & Advanced Research Tech

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/493,702

(22) Filed: Jan. 28, 2000

Related U.S. Application Data

(60) Provisional application No. 60/117,688, filed on Jan. 29, 1999, and provisional application No. 60/118,214, filed on Feb. 1, 1999.

(51) Int. Cl.$^7$ .................................................. A61K 31/355
(52) U.S. Cl. .............................................. 514/449
(58) Field of Search ............................................ 514/449

(56) References Cited

U.S. PATENT DOCUMENTS

| | | | |
|---|---|---|---|
| 5,283,253 | * 2/1994 | Holton et al. | 514/444 |
| 5,455,039 | 10/1995 | Edelman et al. | 424/422 |
| 5,527,532 | 6/1996 | Edelman et al. | 424/422 |
| 5,540,928 | 7/1996 | Edelman et al. | 424/422 |
| 5,616,608 | 4/1997 | Kinsella et al. | 514/449 |
| 5,626,862 | 5/1997 | Brem et al. | 424/426 |
| 5,651,986 | 7/1997 | Brem et al. | 424/484 |
| 5,667,764 | 9/1997 | Kopia et al. | 424/1.45 |
| 5,716,981 | 2/1998 | Hunter et al. | 514/449 |
| 5,733,925 | 3/1998 | Kunz et al. | 514/449 |
| 5,766,584 | 6/1998 | Edelman et al. | 424/93.7 |
| 5,770,609 | 6/1998 | Grainger et al. | 514/319 |
| 5,811,447 | 9/1998 | Kunz et al. | 514/411 |
| 5,886,026 | 3/1999 | Hunter et al. | 514/449 |
| 5,916,913 | * 6/1999 | Joseph | 514/449 |
| 5,981,568 | 11/1999 | Kunz et al. | 514/411 |
| 5,994,341 | 11/1999 | Hunter et al. | 514/210 |
| 6,074,659 | 6/2000 | Kunz et al. | 424/423 |

FOREIGN PATENT DOCUMENTS

| | | |
|---|---|---|
| WO 93/11120 | 6/1993 | (WO) . |
| WO 95/03795 | 2/1995 | (WO) . |
| WO 96/25176 | 8/1996 | (WO) . |
| WO 97/33552 | 9/1997 | (WO) . |
| WO 98/43618 | 10/1998 | (WO) . |
| WO 00/41687 | 7/2000 | (WO) . |

OTHER PUBLICATIONS

Axel et al., "Paclitaxel inhibits arterial smooth muscle cell proliferation and migration in vitro and in viv using local drug delivery," *Circulation* 96(2): 636–645, 1997.

Burt et al., "Development of copolymers of poly(D,L–lactide) and methoxypolyethylene glycol as micellar carriers of paclitaxel," *Colloids and Surfaces B: Biointerfaces* 16(1–4): 161–171, 1999.

Komowski et al., "Slow–release taxol coated GRII™ stents reduce neointima formation on a porcine coronanry in–stent restenosis model," *Circulation* 96(8): I–341, abstract #1900, 1997.

Kunert et al., "Paclitaxel inhibits development of restenosis following experimental balloon angioplasty in the rabbit carotid artery," *European Heart Journal XX*(17): 368, 1996.

Zhang et al., "An investigation of the antitumour activity and biodistribution of polymeric micellar paclitaxel," *Cancer Chemother Pharmocol* 40: 81–86, 1997.

Zhang et al., "Development of biodegradable polymeric paste formulations for taxol: an in vitro and in vivo study," *International Journal of Pharmaceutics* 137(2): 199–208, 1996.

Bartoli et al., "In vitro and in vivo antitumoral activity of free and encapsulated taxol," *Journal of Microencapsulation* 7(2): 191–197, 1990.

Walter et al., "Interstitial Taxol Delivered from a Biodegradable Polymer Implant angainst Experimental malignant Glimoa," *Cancer Research* 51: 2207–2212, Apr. 15, 1994.

Sollott et al., "Taxol Inhibits Neointimal Smooth Muscle Cell Accumulation after Angioplasty in the Rat," *Journal of Clinical Investigation* 95: 1869–1876, Apr. 1995.

Suh et al., "Regulation of smooth muscle cell proliferation using paclitaxel–loaded poly(ethylene oxide)–poly (lactide/glycolide) nanospheres," *J. Biomed. Mater. Res.* 42(2): 331–338, 1998.

* cited by examiner

Primary Examiner—Raymond Henley, III
(74) Attorney, Agent, or Firm—Seed IP Law Group

(57) ABSTRACT

Methods and compositions are provided for intra-pericardial administration of anti-microtubule agents, suitable for use in treating or preventing a variety of diseases of the pericardium, heart, or, coronary vasculature.

6 Claims, 10 Drawing Sheets

Intrapericardial Micellar
Paclitaxel - Treatment Protocol

Intrapericardial Micellar Paclitaxel
(Swine Coronary Artery Balloon Injury Model)

Control Micelles

Neointimal Hyperplasia
(28 days post-injury)

50 mg Micellar Paclitaxel

Singleinterpericardial infusion
(28 days post-injury)

INTRAPERICARDIAL DELIVERY OF ANTI-MICROTUBULE AGENTS

CROSS-REFERENCE TO RELATED APPLICATIONS

This application claims priority to U.S. Provisional Patent Application No. 60/117,688, filed Jan. 29, 1999; and U.S. Provisional Patent Application No. 60/118,214, filed Feb. 1, 1999, which applications are incorporated by reference in their entirety.

TECHNICAL FIELD

The present invention relates generally to compositions, methods and devices for administering intra-pericardially anti-microtubule agents.

BACKGROUND OF THE INVENTION

Restenosis is a form of chronic vascular injury leading to vessel wall thickening and loss of blood flow to the tissue supplied by the blood vessel. It occurs in response to vascular reconstructive procedures, including virtually any manipulation which attempts to relieve vessel obstructions, and is the major factor limiting the effectiveness of invasive treatments for vascular diseases. Restenosis has been a major challenge to cardiovascular research for the past 15 years. According to 1994 estimates (U.S. Heart and Stroke Foundation), over 60 million Americans have one or more forms of cardiovascular disease. These diseases claimed approximately 1 million lives in the same year (41% of all deaths in the United States) and are considered the leading cause of death and disability in the developed world.

The present invention provides compositions and methods for intrapericardially delivering an anti-microtubule agent so that disease within the pericardium, heart, or coronary vasculature (e.g., restenosis, primary stenosis, or, atherosclerosis) may be treated or prevented. These compositions and methods address the problems associated with the existing procedures, offer significant advantages when compared to existing procedures, and further provides other, related advantages.

SUMMARY OF THE INVENTION

Briefly stated, the present invention provides methods for administering intrapericardially an anti-microtubule agent, suitable for treating or preventing disease of the pericardium, heart, or, coronary vasculature. Representative examples of such agents include taxanes (e.g., paclitaxel and docetaxel), campothecin, eleutherobin, sarcodictyins, epothilones A and B, discodermolide, deuterium oxide ($D_2O$), hexylene glycol (2-methyl-2,4-pentanediol), tubercidin (7-deazaadenosine), LY290181 (2-amino-4-(3-pyridyl)-4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Within other embodiments, the anti-microtubule agent is formulated to further comprise a polymer.

Within certain embodiments of the invention, the anti-microtubule agents may be formulated along with other compounds or compositions, such as, for example, an ointment, cream, lotion, gel, spray, foam, mousse, coating, wrap, paste, barrier, implant, microsphere, microparticle, film or the like. Within certain embodiments, the compound or composition may function as a carrier, which may be either polymeric, or non-polymeric. Representative examples of polymeric carriers include poly(ethylene-vinyl acetate), copolymers of lactic acid and glycolic acid, poly (caprolactone), poly (lactic acid), copolymers of poly (lactic acid) and poly (caprolactone), gelatin, hyaluronic acid, collagen matrices, celluloses and albumen. Representative examples of other suitable carriers include, but are not limited to ethanol; mixtures of ethanol and glycols (e.g., ethylene glycol or propylene glycol); mixtures of ethanol and isopropyl myristate or ethanol, isopropyl myristate and water (e.g., 55:5:40); mixtures of ethanol and eineol or D-limonene (with or without water); glycols (e.g., ethylene glycol or propylene glycol) and mixtures of glycols such as propylene glycol and water, phosphatidyl glycerol, dioleoylphosphatidyl glycerol, Transcutol®, or terpinolene; mixtures of isopropyl myristate and 1-hexyl-2-pyrrolidone, N-dodecyl-2-piperidinone or 1-hexyl-2-pyrrolidone.

These and other aspects of the present invention will become evident upon reference to the following detailed description and attached drawings. In addition, various references are set forth below which describe in more detail certain procedures, devices or compositions, and are therefore incorporated by reference in their entirety.

DETAILED DESCRIPTION OF THE INVENTION

Figure 1:
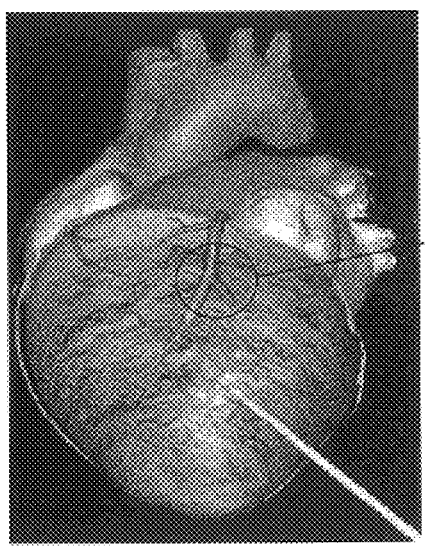
FIGS. 1 and 1A are graphic illustrations of one representative animal model which utilized balloon injury of the LAD or LC.

Prior to setting forth the invention, it may be helpful to an understanding thereof to set forth definitions of certain terms that will be used hereinafter.

"Anti-microtubule Agents" should be understood to include any protein, peptide, chemical, or other molecule which impairs the function of microtubules, for example, through the prevention or stabilization of polymerization. A wide variety of methods may be utilized to determine the anti-microtubule activity of a particular compound, including for example, assays described by Smith et al. (*Cancer Lett* 79(2):213–219, 1994) and Mooberry et al., (*Cancer Lett.* 96(2):261–266, 1995).

As noted above, the present invention provides methods for treating or preventing disease of the pericardium, heart, or coronary vasculature (e.g., stenosis, restenosis, or atherosclerosis), comprising the step of administering to the pericardium, heart or, coronary vasculature an anti-microtubule agent. Briefly, a wide variety of anti-microtubule agents may be delivered, either with or without a carrier (e.g., a polymer or ointment), in order to treat or prevent disease. Representative examples of such agents include taxanes (e.g., paclitaxel (discussed in more detail below) and docetaxel) (Schiff et al., *Nature* 277: 665–667, 1979; Long and Fairchild, *Cancer Research* 54: 4355–4361, 1994; Ringel and Horwitz, *J. Natl. Cancer Inst.* 83(4): 288–291, 1991; Pazdur et al., *Cancer Treat. Rev.* 19(4): 351–386, 1993), campothecin, eleutherobin (e.g., U.S. Pat. No. 5,473,057), sarcodictyins (including sarcodictyin A), epothilones A and B (Bollag et al., *Cancer Research* 55: 2325–2333, 1995), discodermolide (tér Haar et al., *Biochemistry* 35: 243–250, 1996), deuterium oxide ($D_2O$) (James and Lefebvre, *Genetics* 130(2): 305–314, 1992; Sollott et al., *J. Clin. Invest.* 95: 1869–1876, 1995), hexylene glycol (2-methyl-2,4-pentanediol) (Oka et al., *Cell Struct. Funct.* 16(2): 125–134, 1991), tubercidin (7-deazaadenosine) (Mooberry et al., *Cancer Lett.* 96(2): 261–266, 1995), LY290181 (2-amino-4-(3-pyridyl)-4H-naphtho(1,2-b) pyran-3-cardonitrile) (Panda et al., *J. Biol. Chem.* 272(12): 7681–7687, 1997; Wood et al., *Mol. Pharmacol.* 52(3): 437–444, 1997), aluminum fluoride (Song et al., *J. Cell. Sci. Suppl.* 14: 147–150, 1991), ethylene glycol bis-(succinimidylsuccinate) (Caplow and Shanks, *J. Biol. Chem.* 265(15): 8935–8941, 1990), glycine ethyl ester (Mejillano et al., *Biochemistry* 31(13): 3478–3483, 1992), nocodazole (Ding et al., *J. Exp. Med.* 171(3): 715–727, 1990; Dotti et al., *J. Cell Sci. Suppl.* 15: 75–84, 1991; Oka et al., *Cell Struct. Funct.* 16(2): 125–134, 1991; Weimer et al., *J. Cell. Biol.* 136(1), 71–80, 1997), cytochalasin B (Illinger et al., *Biol. Cell* 73(2–3): 131–138, 1991), colchicine and CI 980 (Allen et al., *Am. J. Physiol.* 261(4 Pt. 1) L315–L321, 1991; Ding et al., *J. Exp. Med.* 171(3): 715–727, 1990; Gonzalez et al., *Exp. Cell. Res.* 192(1): 10–15, 1991; Stargell et al., *Mol. Cell. Biol.* 12(4): 1443–1450, 1992; Garcia et al., *Antican. Drugs* 6(4): 533–544, 1995), colcemid (Barlow et al., *Cell. Motil. Cytoskeleton* 19(1): 9–17, 1991; Meschini et al., *J Microsc.* 176(Pt. 3): 204–210, 1994; Oka et al., *Cell Struct. Funct.* 16(2): 125–134, 1991), podophyllotoxin (Ding et al., *J. Exp. Med* 171(3): 715–727, 1990), benomyl (Hardwick et al., *J. Cell. Biol.* 131(3): 709–720, 1995; Shero et al., *Genes Dev.* 5(4): 549–560, 1991), oryzalin (Stargell et al., *Mol. Cell. Biol.* 12(4): 1443–1450, 1992), majusculamide C (Moore, *J. Ind. Microbiol.* 16(2): 134–143, 1996), demecolcine (Van Dolah and Ramsdell, *J. Cell. Physiol.* 166(1): 49–56, 1996; Wiemer et al., *J. Cell. Biol.* 136(1): 71–80, 1997), methyl-2-benzimidazolecarbamate (MBC) (Brown et al., *J. Cell. Biol.* 123(2): 387–403, 1993), LY195448 (Barlow & Cabral, *Cell Motil. Cytoskel.* 19: 9–17, 1991), subtilisin (Saoudi et al., *J. Cell Sci.* 108: 357–367, 1995), 1069C85 (Raynaud et al., *Cancer Chemother. Pharmacol.* 35: 169–173, 1994), steganacin (Hamel, *Med Res. Rev.* 16(2): 207–231, 1996), combretastatins (Hamel, *Med Res. Rev.* 16(2): 207–231, 1996), curacins (Hamel, *Med Res. Rev.* 16(2): 207–231, 1996), estradiol (Aizu-Yokata et al., *Carcinogen.* 15(9): 1875–1879, 1994), 2-methoxyestradiol (Hamel, *Med Res. Rev.* 16(2): 207–231, 1996), flavanols (Hamel, *Med Res. Rev.* 16(2): 207–231, 1996), rotenone (Hamel, *Med Res. Rev.* 16(2): 207–231, 1996), griseofulvin (Hamel, *Med. Res. Rev.* 16(2): 207–231, 1996), vinca alkaloids, including vinblastine and vincristine (Ding et al., *J. Exp. Med* 171(3): 715–727, 1990; Dirk et al., *Neurochem. Res.* 15(11): 1135–1139, 1990; Hamel, *Med Res. Rev.* 16(2): 207–231, 1996; Illinger et al., *Biol. Cell* 73(2–3): 131–138, 1991; Wiemer et al., *J. Cell. Biol.* 136(1): 71–80, 1997), maytansinoids and ansamitocins (Hamel, *Med. Res. Rev.* 16(2): 207–231, 1996), rhizoxin (Hamel, *Med. Res. Rev.* 16(2): 207–231, 1996), phomopsin A (Hamel, *Med. Res. Rev.* 16(2): 207–231, 1996), ustiloxins (Hamel, *Med. Res. Rev.* 16(2): 207–231, 1996), dolastatin 10 (Hamel, *Med. Res. Rev.* 16(2): 207–231, 1996), dolastatin 15 (Hamel, *Med. Res. Rev.* 16(2): 207–231, 1996), halichondrins and halistatins (Hamel, *Med. Res. Rev.* 16(2): 207–231, 1996), spongistatins (Hamel, *Med Res. Rev.* 16(2): 207–231, 1996), cryptophycins (Hamel, *Med. Res. Rev.* 16(2): 207–231, 1996), rhazinilam (Hamel, *Med. Res. Rev.* 16(2): 207–231, 1996), betaine (Hashimoto et al., *Zool. Sci.* 1: 195–204, 1984), taurine (Hashimoto et al., *Zool. Sci.* 1: 195–204, 1984), isethionate (Hashimoto et al., *Zool. Sci.* 1: 195–204, 1984), HO-221 (Ando et al., *Cancer Chemother. Pharmacol.* 37: 63–69, 1995), adociasulfate-2 (Sakowicz et al., *Science* 280: 292–295, 1998), estramustine (Panda et al., *Proc. Natl. Acad. Sci. USA* 94: 10560–10564, 1997), monoclonal anti-idiotypic antibodies (Leu et al., *Proc. Natl. Acad. Sci. USA* 91(22): 10690–10694, 1994), microtubule assembly promoting protein (taxol-like protein, TALP) (Hwang et al., *Biochem. Biophys. Res. Commun.* 208(3): 1174–1180, 1995), cell swelling induced by hypotonic (190 mosmol/L) conditions, insulin (100 nmol/L) or glutamine (10 mmol/L) (Haussinger et al., *Biochem. Cell. Biol.* 72(1–2): 12–19, 1994), dynein binding (Ohba et al., *Biochim. Biophys. Acta* 1158(3): 323–332, 1993), gibberelin (Mita and Shibaoka, *Protoplasma* 119(1/2): 100–109, 1984), XCHO1 (kinesin-like protein) (Yonetani et al., *Mol. Biol. Cell* 7(suppl): 211A, 1996), lysophosphatidic acid (Cook et al., *Mol. Biol Cell* 6(suppl): 260A, 1995), lithium ion (Bhattacharyya and Wolff, *Biochem. Biophys. Res. Commun.* 73(2): 383–390, 1976), plant cell wall components (e.g., poly-L-lysine and extensin) (Akashi et al., *Planta* 182(3): 363–369, 1990), glycerol buffers (Schilstra et al., *Biochem. J.* 277(Pt. 3): 839–847, 1991; Farrell and Keates, *Biochem. Cell. Biol.* 68(11): 1256–1261, 1990; Lopez et al., *J. Cell. Biochem.* 43(3): 281–291, 1990), Triton X-100 microtubule stabilizing buffer (Brown et al., *J. Cell Sci.* 104(Pt. 2): 339–352, 1993; Safiejko-Mroczka and Bell, *J. Histochem. Cytochem.* 44(6): 641–656, 1996), microtubule associated proteins (e.g, MAP2, MAP4, tau, big tau, ensconsin, elongation factor-1-alpha (EF-1α) and E-MAP-115) (Burgess et al., *Cell Motil. Cytoskeleton* 20(4): 289–300, 1991; Saoudi et al., *J. Cell. Sci.* 108(Pt. 1): 357–367, 1995; Bulinski and Bossler, *J. Cell. Sci.* 107(Pt. 10): 2839–2849, 1994; Ookata et al., *J. Cell Biol.* 128(5): 849–862, 1995; Boyne et al., *J. Comp. Neurol.* 358(2): 279–293, 1995; Ferreira and Caceres, *J. Neurosci.*

11(2): 392–400, 1991; Thurston et al., *Chromosoma* 105(1): 20–30, 1996; Wang et al., *Brain Res. Mol. Brain Res.* 38(2): 200–208, 1996; Moore and Cyr, *Mol. Biol. Cell* 7(suppl): 221-A, 1996; Masson and Kreis, *J. Cell Biol.* 123(2), 357–371, 1993), cellular entities (e.g., histone H1, myelin basic protein and kinetochores) (Saoudi et al., *J. Cell. Sci.* 108(Pt. 1): 357–367, 1995; Simerly et al., *J. Cell Biol.* 111(4): 1491–1504, 1990), endogenous microtubular structures (e.g., axonemal structures, plugs and GTP caps) (Dye et al., *Cell Motil. Cytoskeleton* 21(3): 171–186, 1992; Azhar and Murphy, *Cell Motil. Cytoskeleton* 15(3): 156–161, 1990; Walker et al., *J. Cell Biol.* 114(1): 73–81, 1991; Drechsel and Kirschner, *Curr. Biol.* 4(12): 1053–1061, 1994), stable tubule only polypeptide (e.g., STOP145 and STOP220) (Pirollet et al., *Biochim. Biophys. Acta* 1160(1): 113–119, 1992; Pirollet et al., *Biochemistry* 31(37): 8849–8855, 1992; Bosc et al., *Proc. Natl. Acad. Sci. USA* 93(5): 2125–2130, 1996; Margolis et al., *EMBO J.* 9(12): 4095–4102, 1990) and tension from mitotic forces (Nicklas and Ward, *J. Cell Biol.* 126(5): 1241–1253, 1994), as well as any analogues and derivatives of any of the above. Such compounds can act by either depolymerizing microtubules (e.g., colchicine and vinblastine), or by stabilizing microtubule formation (e.g., paclitaxel).

Within one preferred embodiment of the invention, the therapeutic agent is paclitaxel, a compound which disrupts microtubule formation by binding to tubulin to form abnormal mitotic spindles. Briefly, paclitaxel is a highly derivatized diterpenoid (Wani et al., *J. Am. Chem. Soc.* 93:2325, 1971) which has been obtained from the harvested and dried bark of *Taxus brevifolia* (Pacific Yew) and *Taxomyces Andreanae* and *Endophytic Fungus* of the Pacific Yew (Stierle et al., *Science* 60:214–216, 1993). "Paclitaxel" (which should be understood herein to include prodrugs, analogues and derivatives such as, for example, TAXOL®, TAXOTERE®, Docetaxel, 10-desacetyl analogues of paclitaxel and 3'N-desbenzoyl-3'N-t-butoxy carbonyl analogues of paclitaxel) may be readily prepared utilizing techniques known to those skilled in the art (see e.g., Schiff et al., *Nature* 277:665–667, 1979; Long and Fairchild, *Cancer Research* 54:4355–4361, 1994; Ringel and Horwitz, *J. Natl. Cancer Inst.* 83(4):288–291, 1991; Pazdur et al., *Cancer Treat. Rev.* 19(4):351–386, 1993; WO 94/07882; WO 94/07881; WO 94/07880; WO 94/07876; WO 93/23555; WO 93/10076; WO 94/00156; WO 93/24476; EP 590267; WO 94/20089; U.S. Pat. Nos. 5,294,637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; *Tetrahedron Letters* 35(52):9709–9712, 1994; *J. Med Chem.* 35:4230–4237, 1992; *J. Med. Chem.* 34:992–998, 1991; *J. Natural Prod.* 57(10):1404–1410, 1994; *J. Natural Prod.* 57(11):1580–1583, 1994; *J. Am. Chem. Soc.* 110:6558–6560, 1988), or obtained from a variety of commercial sources, including for example, Sigma Chemical Co., St. Louis, Mo. (T7402 - from *Taxus brevifolia*).

Representative examples of such paclitaxel derivatives or analogues include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di (sodium 1,2-benzenedicarboxylate, 10-desacetoxy-11,12-dihydrotaxol-10,12(18)-diene derivatives, 10-desacetoxytaxol, Protaxol (2'-and/or 7-O-ester derivatives), (2'-and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol, Derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG(5000) carbamate taxol, 2'-benzoyl and 2',7-dibenzoyl taxol derivatives, other prodrugs (2'-acetyltaxol; 2',7-diacetyltaxol; 2'succinyltaxol; 2'-(beta-alanyl)-taxol); 2'gamma-aminobutyryltaxol formate; ethylene glycol derivatives of 2'-succinyltaxol; 2'-glutaryltaxol; 2'-(N,N-dimethylglycyl) taxol; 2'-(2-(N,N-dimethylamino) propionyl)taxol; 2'orthocarboxybenzoyl taxol; 2'aliphatic carboxylic acid derivatives of taxol, Prodrugs {2'(N,N-diethylaminopropionyl)taxol, 2'(N,N-dimethylglycyl)taxol, 7(N,N-dimethylglycyl)taxol, 2',7-di-(N,N-dimethylglycyl) taxol, 7(N,N-diethylaminopropionyl)taxol, 2',7-di(N,N-diethylaminopropionyl)taxol, 2'-(L-glycyl)taxol, 7-(L-glycyl)taxol, 2',7-di(L-glycyl)taxol, 2'-(L-alanyl)taxol, 7-(L-alanyl)taxol, 2',7-di(L-alanyl)taxol, 2'-(L-leucyl)taxol, 7-(L-leucyl)taxol, 2',7-di(L-leucyl)taxol, 2'-(L-isoleucyl) taxol, 7-(L-isoleucyl)taxol, 2',7-di(L-isoleucyl)taxol, 2'-(L-valyl)taxol, 7-(L-valyl)taxol, 2'7-di(L-valyl)taxol, 2'-(L-phenylalanyl)taxol, 7-(L-phenylalanyl)taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2',7-di(L-lysyl)taxol, 2'-(L-glutamyl)taxol, 7-(L-glutamyl) taxol, 2',7-di(L-glutamyl)taxol, 2'-(L-arginyl)taxol, 7-(L-arginyl)taxol, 2',7-di(L-arginyl)taxol}, Taxol analogs with modified phenylisoserine side chains, taxotere, (N-debenzoyl-N-tert-(butoxycaronyl)-10 -deacetyltaxol, and taxanes (e.g., baccatin III, cephalomannine, 10-deacetylbaccatin III, brevifoliol, yunantaxusin and taxusin).

Formulations

As noted above, therapeutic anti-microtubule agents described herein may be formulated in a variety of manners, and thus may additionally comprise a carrier. In this regard, a wide variety of carriers may be selected of either polymeric or non-polymeric origin.

For example, within one embodiment of the invention a wide variety of polymeric carriers may be utilized to contain and/or deliver one or more of the therapeutic agents discussed above, including for example both biodegradable and non-biodegradable compositions. Representative examples of biodegradable compositions include albumin, collagen, gelatin, hyaluronic acid, starch, cellulose (methylcellulose, hydroxypropylcellulose, hydroxypropylmethylcellulose,, hydroxyethylcellulose, carboxymethylcellulose, cellulose acetate phthalate, cellulose acetate succinate, hydroxypropylmethylcellulose phthalate), casein, dextrans, polysaccharides, fibrinogen, poly(D,L lactide), poly(D,L-lactide-coglycolide), poly(glycolide), poly (hydroxybutyrate), poly(alkylcarbonate) and poly (orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) "Polymers in Controlled Drug Delivery" Wright, Bristol, 1987; Arshady, *J. Controlled Release* 17:1–22, 1991; Pitt, *Int. J. Phar.* 59:173–196, 1990; Holland et al., *J. Controlled Release* 4:155–0180, 1986). Representative examples of nondegradable polymers include poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polyproplene, polyamides (nylon 6,6), polyurethane, poly(ester urethanes), poly (ether urethanes), poly(ester-urea), polyethers (poly (ethylene oxide), poly(propylene oxide), Pluronics and poly (tetramethylene glycol)), silicone rubbers and vinyl polymers (polyvinylpyrrolidone, poly(vinyl alcohol), poly (vinyl acetate phthalate). Polymers may also be developed which are either anionic (e.g., alginate, carrageenin, carboxymethyl cellulose and poly(acrylic acid), or cationic (e.g, chitosan, poly-L-lysine, polyethylenimine, and poly (allyl amine)) (see generally, Dunn et al., *J. Applied Polymer Sci.* 50:353–365, 1993; Cascone et al., *J. Materials Sci. Materials in Medicine* 5:770–774, 1994; Shiraishi et al., *Biol. Pharm. Bull.* 16(11):1164–1168, 1993; Thacharodi and Rao, *Int'l J. Pharm.* 120:115–118, 1995; Miyazaki et al., *Int'l J. Pharm.* 118:257–263, 1995). Particularly preferred polymeric carriers include poly(ethylene-vinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with a polyethylene glycol (e.g., MePEG), and blends thereof.

Polymeric carriers can be fashioned in a variety of forms, with desired release characteristics and/or with specific desired properties. For example, polymeric carriers may be fashioned to release a therapeutic agent upon exposure to a specific triggering event such as pH (see e.g., Heller et al., "Chemically Self-Regulated Drug Delivery Systems," in *Polymers in Medicine III*, Elsevier Science Publishers B. V., Amsterdam, 1988, pp. 175–188; Kang et al., *J. Applied Polymer Sci.* 48:343–354, 1993; Dong et al., *J. Controlled Release* 19.171–178, 1992; Dong and Hoffman, *J. Controlled Release* 15:141–152, 1991; Kim et al., *J. Controlled Release* 28:143–152, 1994; Cornejo-Bravo et al., *J. Controlled Release* 33:223–229, 1995; Wu and Lee, *Pharm. Res.* 10(10):1544–1547, 1993; Serres et al., *Pharm. Res.* 13(2):196–201, 1996; Peppas, "Fundamentals of pH- and Temperature-Sensitive Delivery Systems," in Gurny et al. (eds.), *Pulsatile Drug Delivery*, Wissenschaftliche Verlagsgesellschaft mbH, Stuttgart, 1993, pp. 41–55; Doelker, "Cellulose Derivatives," 1993, in Peppas and Langer (eds.), *Biopolymers* I, Springer-Verlag, Berlin). Representative examples of pH-sensitive polymers include poly(acrylic acid) and its derivatives (including for example, homopolymers such as poly(aminocarboxylic acid); poly(acrylic acid); poly(methyl acrylic acid), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water soluble polymer.

Likewise, polymeric carriers can be fashioned which are temperature sensitive (see e.g., Chen et al., "Novel Hydrogels of a Temperature-Sensitive Pluronic Grafted to a Bioadhesive Polyacrylic Acid Backbone for Vaginal Drug Delivery," in *Proceed Intern. Symp. Control. Rel. Bioact. Mater.* 22:167–168, Controlled Release Society, Inc., 1995; Okano, "Molecular Design of Stimuli-Responsive Hydrogels for Temporal Controlled Drug Delivery," in *Proceed Intern. Symp. Control. Rel. Bioact. Mater.* 22:111–112, Controlled Release Society, Inc., 1995; Johnston et al., *Pharm. Res.* 9(3):425–433, 1992; Tung, *Int'l J. Pharm.* 107:85–90, 1994; Harsh and Gehrke, *J. Controlled Release* 17:175–186, 1991; Bae et al., *Pharm. Res.* 8(4):531–537, 1991; Dinarvand and D'Emanuele, *J. Controlled Release* 36:221–227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820–821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822–823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829–830; Kim et al., *Pharm. Res.* 9(3):283–290, 1992; Bae et al., *Pharm. Res.* 8(5):624–628, 1991; Kono et al., *J. Controlled Release* 30:69–75, 1994; Yoshida et al., *J. Controlled Release* 32:97–102, 1994; Okano et al., *J. Controlled Release* 36:125–133, 1995; Chun and Kim, *J. Controlled Release* 38:39–47, 1996; D'Emanuele and Dinarvand, *Int'l J. Pharm.* 118:237–242, 1995; Katono et al., *J. Controlled Release* 16:215–228, 1991; Hoffman, "Thermally Reversible Hydrogels Containing Biologically Active Species," in Migliaresi et al. (eds.), *Polymers in Medicine III*, Elsevier Science Publishers B. V., Amsterdam, 1988, pp. 161–167; Hoffman, "Applications of Thermally Reversible Polymers and Hydrogels in Therapeutics and Diagnostics," in *Third International Symposium on Recent Advances in Drug Delivery Systems*, Salt Lake City, Utah, Feb. 24–27, 1987, pp. 297–305; Gutowska et al., *J. Controlled Release* 22:95–104, 1992; Palasis and Gehrke, *J. Controlled Release* 18:1–12, 1992; Paavola et al., *Pharm. Res.* 12(12):1997–2002, 1995).

Representative examples of thermogelling polymers, and their gelatin temperature (LCST (° C.)) include homopolymers such as poly(N-methyl-N-n-propylacrylamide), 19.8; poly(N-n-propylacrylamide), 21.5; poly(N-methyl-N-isopropylacrylamide), 22.3; poly(N-n-propylmethacrylamide), 28.0; poly(N-isopropylacrylamide), 30.9; poly(N, n-diethylacrylamide), 32.0; poly(N-isopropylmethacrylamide), 44.0; poly(N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; poly(N-ethylacrylamide), 72.0. Moreover thermogelling polymers may be made by preparing copolymers between (among) monomers of the above, or by combining such homopolymers with other water soluble polymers such as acrylmonomers (e.g. acrylic acid and derivatives thereof such as methylacrylic acid, acrylate and derivatives thereof such as butyl methacrylate, acrylamide, and N-n-butyl acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, and Pluronics such as F-127, 10–15° C.; L-122, 19° C.; L-92, 26° C.; L-81, 20° C.; and L-61, 24° C.

A wide variety of forms may be fashioned by the polymeric carriers of the present invention, including for example, rod-shaped devices, pellets, slabs, or capsules (see e.g., Goodell et al., *Am. J. Hosp. Pharm.* 43:1454–1461, 1986; Langer et al., "Controlled release of macromolecules from polymers", in *Biomedical Polymers, Polymeric Materials and Pharmaceuticals for Biomedical Use,* Goldberg, E. P., Nakagim, A. (eds.) Academic Press, pp. 113–137, 1980; Rhine et al., *J. Pharm. Sci.* 69:265–270, 1980; Brown et al., *J. Pharm. Sci.* 72:1181–1185, 1983; and Bawa et al., *J. Controlled Release* 1:259–267, 1985). Therapeutic agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes, threads of various size, films and sprays.

Preferably, therapeutic compositions of the present invention are fashioned in a manner appropriate to the intended use. Within certain aspects of the present invention, the therapeutic composition should be biocompatible, and release one or more therapeutic agents over a period of several days to months. For example, "quick release" or "burst" therapeutic compositions are provided that release greater than 10%, 20%, or 25% (w/v) of a therapeutic agent (e.g., paclitaxel) over a period of 7 to 10 days. Such "quick release" compositions should, within certain embodiments, be capable of releasing chemotherapeutic levels (where applicable) of a desired agent. Within other embodiments, "low release" therapeutic compositions are provided that release less than 1% (w/v) of a therapeutic agent over a period of 7 to 10 days. Further, therapeutic compositions of the present invention should preferably be stable for several months and capable of being produced and maintained under sterile conditions.

Within certain aspects of the present invention, therapeutic compositions may be fashioned in any size ranging from 50 nm to 500 µm, depending upon the particular use. Alternatively, such compositions may also be readily applied as a "spray", which solidifies into a film or coating. Such sprays may be prepared from microspheres of a wide array of sizes, including for example, from 0.1 µm to 3 µm, from 10 µm to 30 µm, and from 30 µm to 100 µm.

Therapeutic compositions of the present invention may also be prepared in a variety of "paste" or gel forms. For example, within one embodiment of the invention, therapeutic compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" may be readily made given the disclosure provided herein.

Formualtion and Administration

As noted above, anti-microtubule agents of the present invention may be formulated in a variety of forms suitable for administration. Further, the compositions of the present invention may be formulated to contain more than one anti-microtubule agents, to contain a variety of additional compounds, to have certain physical properties (e.g., elasticity, a particular melting point, or a specified release rate). Within certain embodiments of the invention, compositions may be combined in order to achieve a desired effect (e.g., several preparations of microspheres may be combined in order to achieve both a quick and a slow or prolonged release of one or more anti-microtubule agents).

Anti-microtubule agents may be administered either alone, or in combination with pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

The anti-microtubule agent can be administered in a dosage which achieves a statistically significant result. In one embodiment, an antimicrotubule agent such as paclitaxel is administered at a dosage ranging from 100 ug to 50 mg, depending on the mode of administration and the type of carrier, if any for delivery. For treatment of restenosis, a single treatment may be provided before, during or after balloon angioplasty or stenting. For the treatment of instent restenosis, the anti-microtubule agent may be administered directly to prevent closure of the stented vessel. For the treatment of atherosclerosis, an anti-microtubule agent such as paclitaxel may be administered periodically, e.g., once every few months. In the case of cardiac transplantation, the anti-microtubule agent may be delivered in a slow release form that delivers from 1 to 75 mg/m$^2$ (preferably 10 to 50 mg/m$^2$) over a selected period of time. With any of these embodiments, the anti-microtubule agent (e.g., paclitaxel) may be administered along with other therapeutics.

Pericardial administration may be accomplished by a variety of manners including, for example, direct injection (preferably with ultrasound, CT, fluoroscopic, MRI or endoscopic guidance). (See e.g., U.S. Pat. Nos. 5,840,059 and 5,797,870). Within certain embodiments, a Saphenous Vein Harvester such as GSI's ENDOsaph, or Comedicus Inc,.' PerDUCER (Pericardial Access Device) may be utilized to administer the desired anti-microtubule agent (e.g., paclitaxel).

Within one embodiment, the antimicrotubule agent or composition (e.g., paclitaxel and a polymer) may be delivered trans-myocardially through the right or left ventricle.

Within other embodiments, the antimicrotubule agent or composition (e.g., paclitaxel and a polymer) may be administered trans-myocardially through the right atrium. (See, e.g., U.S. Pat. Nos. 5,797,870 and 5,269,326). Briefly, the right atrium lies between the pericardium and the epicardium. An appropriate catheter is guided into the right atrium and positioned parallel with the wall of the pericardium. This positioning allows piercing of the right atrium (either by the catheter, or by an instrument that is passed within the catheter), without risk of damage to either the pericardium or the epicardium. The catheter can then be passed into the pericardial space, or an instrument passed through the lumen of the catheter into the pericardial space.

Alternatively, access to the pericardium, heart, or coronary vasculature may be gained operatively, by, for example, sub-xiphoid entry, a thoracotomy, or, open heart surgery. Preferably, the thoracotomy should be minimal, through an intercostal space for example. Fluoroscopy, or ultrasonic visualization may be utilized to assist in any of these procedures.

The following examples are offered by way of illustration, and not by way of limitation.

EXAMPLES

Example 1

Manufacture of and Use of Dibock Co-polymers for Formulating the Delivery of Anti-microtubule Agents

One formulation for paclitaxel is comprised of amphiphilic diblock copolymers which in aqueous solutions form micelles consisting of a hydrophobic core and a hydrophilic shell in water. Briefly, diblock copolymers of poly(DL-lactide)-block-methoxy polyethylene glycol (PDLLA-MePEG), polycaprolactone-block methoxy polyethylene glycol (PCL-MePEG) and poly(DL-lactide-co-caprolactone)-block-methoxy polyethylene glycol (PDLLACL-MePEG) can be synthesized using a bulk melt polymerization procedure, or similar methods. Briefly, given amounts of monomers DL-lactide, caprolactone and methoxy polyethylene glycols with different molecular weights were heated (130° C.) to melt under the bubbling of nitrogen and stirred. The catalyst stannous octoate (0.2% w/w) was added to the molten monomers. The polymerization was carried out for 4 hours. The molecular weights, critical micelle concentrations and the maximum paclitaxel loadings were measured with GPC, fluorescence, and solubilization testing, respectively. High paclitaxel carrying capacities were obtained. The ability of solubilizing paclitaxel depends on the compositions and concentrations of the copolymers. PDLLA-MePEG gave the most stable solubilized paclitaxel.

The strong association within the internal core of the polymeric micelles presents a high capacity environment for carrying hydrophobic drugs such as paclitaxel. The drugs can be covalently coupled to block copolymers to form a micellar structure or can be physically incorporated within the hydrophobic cores of the micelles. The mechanisms of drug release from the micelles include diffusion from the core and the exchange between the single polymer chains and the micelles. The small size of the micelles (normally less than 100 nm) will eliminate the difficulties associated with injecting larger particles.

Example 2

Procedure for Producing Thermopaste

Five grams of polycaprolactone mol. wt. 10,000 to 20,000; (Polysciences, Warrington Penn. USA) a 20 ml glass scintillation vial which was placed into a 600 ml beaker containing 50 ml of water weighed. The beaker was gently heated to 65° C. and held at that temperature for 20 minutes until the polymer melted. A known weight of paclitaxel, or other angiogenesis inhibitor was thoroughly mixed into the melted polymer at 65° C. The melted polymer was poured into a prewarmed (60° C. oven) mould and allowed to cool until the polymer solidified. The polymer was cut into small pieces (approximately 2 mm by 2 mm in size) and was placed into a 1 ml glass syringe.

The glass syringe was then placed upright (capped tip downwards) into a 500 ml glass beaker containing distilled water at 65° C. (corning hot plate) until the polymer melted completely. The plunger was then inserted into the syringe to compress the melted polymer into a sticky mass at the tip end of the barrel. The syringe was capped and allowed to cool to room temperature.

For application, the syringe was reheated to 60° C. and administered as a liquid which solidified when cooled to body temperature.

Example 3

Modification of Paclitaxel Release from Thermopaste Using PDLLA-PEG-PDLLA and Low Molecular Weight POLY(D,L, LACTIC ACID)

A. Preparation of PDLLA-PEG-PDLLA and Low Molecular Weight PDLLA

DL-lactide was purchased from Aldrich. Polyethylene glycol (PEG) with molecular weight 8,000, stannous octoate, and DL-lactic acid were obtained from Sigma. Poly-ε-caprolactone (PCL) with molecular weight 20,000 was obtained from Birmingham Polymers (Birmingham, Ala.). Paclitaxel was purchased from Hauser Chemicals (Boulder, Colo.). Polystyrene standards with narrow molecular weight distributions were purchased from Polysciences (Warrington, Pa.). Acetonitrile and methylene chloride were HPLC grade (Fisher Scientific).

The triblock copolymer of PDLLA-PEG-PDLLA was synthesized by a ring opening polymerization. Monomers of DL-lactide and PEG in different ratios were mixed and 0.5 wt % stannous octoate was added. The polymerization was carried out at 150° C. for 3.5 hours. Low molecular weight PDLLA was synthesized through polycondensation of DL-lactic acid. The reaction was performed in a glass flask under the conditions of gentle nitrogen purge, mechanical stirring, and heating at 180° C. for 1.5 hours. The PDLLA molecular weight was about 800 measured by titrating the carboxylic acid end groups.

B. Manufacture of Paste Formulations

Paclitaxel at loadings of 20% or 30% was thoroughly mixed into either the PDLLA-PEG-PDLLA copolymers or blends of PDLLA:PCL 90:10, 80:20 and 70:30 melted at about 60° C. The paclitaxel-loaded pastes were weighed into 1 ml syringes and stored at 4° C.

C. Characterization of PDLLA-PEG-PDLLA and the Paste Blends

The molecular weights and distributions of the PDLLA-PEG-PDLLA copolymers were determined at ambient temperature by GPC using a Shimadzu LC-10AD HPLC pump and a Shimadzu RID-6A refractive index detector (Kyoto, Japan) coupled to a $10^4$ Å Hewlett Packard P1 gel column. The mobile phase was chloroform with a flow rate of 1 ml/minute. The injection volume of the sample was 20 μl at a polymer concentration of 0.2% (w/v). The molecular weights of the polymers were determined relative to polystyrene standards. The intrinsic viscosity of PDLLA-PEG-PDLLA in $CHCl_3$ at 25° C. was measured with a Cannon-Fenske viscometer.

Thermal analysis of the copolymers was carried out by differential scanning calorimetry (DSC) using a TA Instruments 2000 controller and DuPont 910 S DSC (Newcastle, Del.). The heating rate was 10° C./min and the copolymer and paclitaxel/copolymer matrix samples were weighed (3–5 mg) into crimped open aluminum sample pans.

$^1H$ nuclear magnetic resonance (NMR) was used to determine the chemical composition of the polymer. $^1H$ NMR spectra of paclitaxel-loaded PDLLA-PEG-PDLLA were obtained in $CDCl_3$ using an NMR instrument (Bruker, AC-200E) at 200 MHz. The concentration of the polymer was 1–2%.

The morphology of the paclitaxel/PDLLA-PEG-PDLLA paste was investigated using scanning electron microscopy (SEM) (Hitachi F-2300). The sample was coated with 60% Au and 40% Pd (thickness 10–15 nm) using a Hummer instrument (Technics, USA).

D. In Vitro Release of Paclitaxel

A small pellet of 20% paclitaxel-loaded PDLLA:PCL paste (about 2 mg) or a cylinder (made by extruding molten paste through a syringe) of 20% paclitaxel-loaded PDLLA-PEG-PDLLA paste were placed into capped 14 ml glass tubes containing 10 ml phosphate buffered saline (pH 7.4) with 0.4 g/L albumin. The tube was incubated at 37° C. with gentle rotational mixing. The supernatant was withdrawn periodically for paclitaxel analysis and replaced with fresh PBS/albumin buffer. The supernatant (10 ml) was extracted with 1 ml methylene chloride. The water phase was decanted and the methylene chloride phase was dried under a stream of nitrogen at 60° C. The dried residue was reconstituted in a 40:60 water:acetonitrile mixture and centrifuged at 10,000g for about 1 min. The amount of paclitaxel in the supernatant was then analyzed by HPLC. HPLC analysis was performed using a 110A pump and C-8 ultrasphere column (Beckman), and a SPD-6A UV detector set at 232 nm, a SIL-9A autoinjector and a C-R3A integrator (Shimadzu). The injection volume was 20 $\mu$l and the flow rate was 1 ml/minute. The mobile phase was 58% acetonitrile, 5% methanol, and 37% distilled water.

E. Results and Discussion

The molecular weight and molecular weight distribution of PDLLA-PEG-PDLLA, relative to polystyrene standards, were measured by GPC. The intrinsic viscosity of the copolymer in $CHCl_3$ at 25° C. was determined using a Canon-Fenske viscometer. The molecular weight and intrinsic viscosity decreased with increasing PEG content. The polydispersities of PDLLA-PEG-PDLLA with PEG contents of 10–40% were from 2.4 to 3.5. However, the copolymer with 70% PEG had a narrow molecular weight distribution with a polydispersity of 1.21. This might be due to a high PEG content reducing the chance of side reactions such as transesterfication which results in a wide distribution of polymer molecular weights. Alternatively, a coiled structure of the hydrophobic-hydrophilic block copolymers may result in an artificial low polydispersity value.

The PEG and PDLLA-PEG-PDLLA with PEG contents of 70% and 40% showed endothermic peaks with decreasing enthalpy and temperature as the PEG content of the copolymer decreased. The endothermic peaks in the copolymers of 40% and 70% PEG were probably due to the melting of the PEG region, indicating the occurrence of phase separation. While pure PEG had a sharp melting peak, the copolymers of both 70% and 40% PEG showed broad peaks with a distinct shoulder in the case of 70% PEG. The broad melting peaks may have resulted from the interference of PDLLA with the crystallization of PEG. The shoulder in the case of 70% PEG might represent the glass transition of the PDLLA region. No thermal changes occurred in the copolymers with PEG contents of 10%, 20% and 30% in a temperature range of 10–250° C., indicating that no significant crystallization (therefore may be the phase separation) had occurred.

DSC thermograms of PDLLA:PCL (70:30, 80:20, 90:10) blends without paclitaxel or with 20% paclitaxel showed an endothermic peak at about 60° C., resulting from the melting of PCL. Due to the amorphous nature of the PDLLA and its low molecular weight (800), melting and glass transitions of PDLLA were not observed. No thermal changes due to the recrystallization or melting of paclitaxel was observed.

PDLLA-PEG-PDLLA copolymers of 20% and 30% PEG content were selected as optimum formulation materials for the paste for the following reasons: PDLLA-PEG-PDLLA of 10% PEG could not be melted at a temperature of about 60° C.; the copolymers of 40% and 70% PEG were readily melted at 60° C., and the 20% and 30% PEG copolymer became a viscous liquid between 50° C. to 60° C.; and the swelling of 40% and 70% PEG copolymers in water was very high resulting in rapid dispersion of the pastes in water.

Example 4

Preparation of Polymeric Compositions Containing Water Soluble Additives and Paclitaxel A. Preparation of Polymeric Compositions Microparticles of co-precipitates of paclitaxel/additive were prepared and subsequently added to PCL to form pastes. Briefly, paclitaxel (100 mg) was dissolved in 0.5 ml of ethanol (95%) and mixed with the additive (100 mg) previously dissolved or dispersed in 1.0 ml of distilled water. The mixture was triturated until a smooth paste was formed. The paste was spread on a Petri dish and air-dried overnight at 37° C. The dried mass was pulverized using a mortar and pestle and passed through a mesh #140 (106 $\mu$m) sieve (Endecotts Test Sieves Ltd., London, England). The microparticles (40%) were then incorporated into molten PCL (60%) at 65° C. corresponding to a 20% loading of paclitaxel. The additives used in the study were gelatin (Type B, 100 bloom, Fisher Scientific), methylcellulose, (British Drug Houses), dextran, T500 (Pharmacia, Sweden), albumin (Fisher Scientific), and sodium chloride (Fisher Scientific). Microparticles of paclitaxel and gelatin or albumin were prepared as described above but were passed through a mesh #60 (270 $\mu$m) sieve (Endecotts Test Sieves Ltd., London, England) to evaluate the effect of microparticle size on the release of paclitaxel from the paste. Pastes were also prepared to contain 10, 20 or 30% gelatin and 20% paclitaxel in PCL to study the effect of the proportion of the additive on drug release. Unless otherwise specified, pastes containing 20% paclitaxel dispersed in PCL were prepared to serve as controls for the release rate studies.

B. Drug Release Studies

Approximately a 2.5 mg pellet of paclitaxel-loaded paste was suspended in 50 ml of 10 mM PBS (pH 7.4) in screw-capped tubes. The tubes were tumbled end-over-end at 37° C. and at given time intervals 49.5 ml of supernatant was removed, filtered through a 0.45 $\mu$m membrane filter and retained for paclitaxel analysis. An equal volume of PBS was replaced in each tube to maintain sink conditions throughout the study. For analysis, the filtrates were extracted with 3×1 ml dichloromethane (DCM), the DCM extracts evaporated to dryness under a stream of nitrogen and redissolved in 1 ml acetonitrile. The analysis was by HPLC using a mobile phase of water:methanol:acetonitrile (37:5:58:) at a flow rate of 1 ml/minute (Beckman Isocratic Pump), a C18 reverse phase column (Beckman), and UV detection (Shimadzu SPD A) at 232 nm.

C. Swelling Studies

Paclitaxel/additive/PCL pastes, prepared using paclitaxel-additive microparticles of mesh size #140 (and #60 for gelatin only), were extruded to form cylinders, pieces were cut, weighed and the diameter and length of each piece were measured using a micrometer (Mitutoyo Digimatic). The pieces were suspended in distilled water (10 ml) at 37° C. and at predetermined intervals the water was discarded and the diameter and the length of the cylindrical pieces were measured and the samples weighed. The morphology of the samples (before and after suspending in water) was examined using scanning electron microscopy (SEM) (Hitachi F-2300). The samples were coated with 60% Au and 40% Pd (thickness 10–15 nm) using a Hummer Instrument (Technics, USA).

D. Chick Embryo Chorioallantoic Membrane (CAM) Studies

Fertilized, domestic chick embryos were incubated for 4 days prior to shell-less culturing. The egg contents were incubated at 90% relative humidity and 3% $CO_2$ and on day 6 of incubation, 1 mg pieces of the paclitaxel-loaded paste (containing 6% paclitaxel, 24% gelatin and 70% PCL) or control (30% gelatin in PCL) pastes were placed directly on the CAM surface. After a 2-day exposure the vasculature was examined using a stereomicroscope interfaced with a video camera; the video signals were then displayed on a computer and video printed.

E. Results and Discussion

Microparticles of co-precipitated paclitaxel and gelatin or albumin were hard and brittle and were readily incorporated into PCL, while the other additives produced soft particles which showed a tendency to break up during the preparation of the paste.

The release of paclitaxel from PCL with or without additives followed a biphasic release pattern; initially, there was a faster drug release rate followed by a slower drug release of the drug. The initial period of faster release rate of paclitaxel from the pastes was thought to be due to dissolution of paclitaxel located on the surface or diffusion of paclitaxel from the superficial regions of the paste. The subsequent slower phase of the release profiles may be attributed to a decrease in the effective surface area of the drug particles in contact with the buffer, a slow ingress of the buffer into the polymer matrix or an increase in the mean diffusion paths of the drug through the polymer matrix.

Example 5

Procedure for Producing Nanopaste

Nanopaste is a suspension of microspheres in a hydrophilic gel. Within one aspect of the invention, the gel or paste can be smeared over tissue as a method of locating drug-loaded microspheres close to the target tissue. Being water based, the paste soon becomes diluted with bodily fluids causing a decrease in the stickiness of the paste and a tendency of the microspheres to be deposited on nearby tissue. A pool of microsphere encapsulated drug is thereby located close to the target tissue.

Reagents and equipment which were utilized within these experiments include glass beakers, Carbopol 925 (pharmaceutical grade, Goodyear Chemical Co.), distilled water, sodium hydroxide (1 M) in water solution, sodium hydroxide solution (5 M) in water solution, microspheres in the 0.1 lm to 3 lm size range suspended in water at 20% w/v (see previous).

1. Preparation of 5% w/v Carbopol Gel

A sufficient amount of carbopol was added to 1 M sodium hydroxide to achieve a 5% w/v solution. To dissolve the carbopol in the 1 M sodium hydroxide, the mixture was allowed to sit for approximately one hour. During this time period, the mixture was stirred and, after one hour, the pH was adjusted to 7.4 using 5 M sodium hydroxide until the carbopol was fully dissolved. Once a pH of 7.4 was achieved, the gel was covered and allowed to sit for 2 to 3 hours.

2. Procedure for Producing Nanopaste

A sufficient amount of 0.1 $\mu$m to 3 $\mu$m microspheres was added to water to produce a 20% suspension of the microspheres. Carbopol gel (8 ml of the 5% w/v) was placed into a glass beaker and 2 ml of the 20% microsphere suspension was added. The mixture was stirred to thoroughly disperse the microspheres throughout the gel. This mixture was stored at 4° C.

Example 6

Polymeric Compositions with Increased Concentrations of Paclitaxel

PDLLA-MePEG and PDLLA-PEG-PDLLA are block copolymers with hydrophobic (PDLLA) and hydrophilic (PEG or MePEG) regions. At appropriate molecular weights and chemical composition, they may form tiny aggregates of hydrophobic PDLLA core and hydrophilic MePEG shell. Paclitaxel can be loaded into the hydrophobic core, thereby providing paclitaxel with an increased "solubility".

A. Materials

D,L-lactide was purchased from Aldrich, Stannous octoate, poly (ethylene glycol) (mol. wt. 8,000), MePEG (mol. wt. 2,000 and 5,000) were from Sigma. MePEG (mol. wt. 750) was from Union Carbide. The copolymers were synthesized by a ring opening polymerization procedure using stannous octoate as a catalyst (Deng et al., *J. Polym. Sci., Polym, Lett.* 28:411–416, 1990; Cohn et al., *J. Biomed, Mater. Res.* 22: 993–1009, 1988).

For synthesizing PDLLA-MePEG, a mixture of DL-lactide/MePEG/stannous octoate was added to a 10 milliliter glass ampoule. The ampoule was connected to a vacuum and sealed with flame. Polymerization was accomplished by incubating the ampoule in a 150° C. oil bath for 3 hours. For synthesizing PDLLA-PEG-PDLLA, a mixture of D,L-lactide/PEG/stannous octoate was transferred into a glass flask, sealed with a rubber stopper, and heated for 3 hours in a 150° C. oven. The starting compositions of the copolymers are given in Tables 1 and 2. In all the cases, the amount of stannous octoate was 0.5%–0.7%.

B. Methods

The polymers were dissolved in acetonitrile and centrifuged at 10,000 g for 5 minutes to discard any non-dissolvable impurities. Paclitaxel acetonitrile solution was then added to each polymer solution to give a solution with paclitaxel (paclitaxel+polymer) of 10% wt. The solvent acetonitrile was then removed to obtain a clear paclitaxel/PDLLA-MePEG matrix, under a stream of nitrogen and 60° C. warming. Distilled water, 0.9% NaCl saline, or 5% dextrose was added at four times weight of the matrix. The matrix was finally "dissolved" with the help of vortex mixing and periodic warming at 60° C. Clear solutions were obtained in all the cases. The particle sizes were all below 50 nm as determined by a submicron particle sizer (NICOMP Model 270). The formulations are given in Table 1.

TABLE 1

Formulations of Paclitaxel/PDLLA-MePEG*

| PDLLA-MePEG | Dissolving Media | Paclitaxel Loading (final paclitaxel concentrate) |
|---|---|---|
| 2000/50/50 | water | 10% (20 mg/ml) |
| 2000/40/60 | water | 10% (20 mg/ml) |
| 2000/50/50 | 0.9% saline | 5% (10 mg/ml) |
| 2000/50/50 | 0.9% saline | 10% (20 mg/ml) |
| 2000/50/50 | 5% dextrose | 10% (10 mg/ml) |
| 2000/50/50 | 5% dextrose | 10% (20 mg/ml) |

In the case of PDLLA-PEG-PDLLA (Table 2), since the copolymers cannot dissolve in water, paclitaxel and the polymer were co-dissolved in acetone. Water or a mixture of water/acetone was gradually added to this paclitaxel polymer solution to induce the formation of paclitaxel/polymer spheres.

TABLE 2

Composition of PDLLA-PEG-PDLLA

| Copolymer Name | Wt. of PEG (g) | Wt. of DL-lactide (g) |
|---|---|---|
| PDLLA-PEG-PDLLA 90/10 | 1 | 9 |
| PDLLA-PEG-PDLLA 80/20 | 2 | 8 |
| PDLLA-PEG-PDLLA 70/30 | 3 | 7 |
| PDLLA-PEG-PDLLA 60/40 | 4 | 6 |
| PDLLA-PEG-PDLLA 30-/70 | 14 | 6 |

*PEG molecular weight. 8,000.

C. Results

Many of the PDLLA-MePEG compositions form clear solutions in water, 0.9% saline, or 5% dextrose, indicating the formation of tiny aggregates in the range of nanometers. Paclitaxel was loaded into PDLLA-MePEG micelles successfully. For example, at % loading (this represents 10 mg paclitaxel in 1 ml paclitaxel/PDLLA-MePEG/aqueous system), a clear solution was obtained from 2000-50/50 and 2000-40/60. The particle size was about 60 nm.

Example 7

Manufacture of Micellar Paciltaxel

Poly(DL-lactide)-block-methoxypolyethylene glycol (PDLLA-block-MePEG) with a MePEG molecular weight of 2000 and a PDLLA:MePEG weight ratio 40:60 is used as the micellar carrier for the solubilization of paclitaxel. PDLLA-MePEG 2000-40/60 (polymer) is an amphiphilic diblock copolymer that dissolves in aqueous solutions to form micelles with a hydrophobic PDLLA core and hydrophilic MePEG shell. Paclitaxel is physically trapped in the hydrophobic PDLLA core to achieve the solubilization.

The polymer was synthesized from the monomers methoxypolyethylene glycol and DL-lactide in the presence of 0.5% w/w stannous octoate through a ring opening polymerization. Stannous octoate acted as a catalyst and participated in the initiation of the polymerization reaction. Stannous octoate forms a number of catalytically reactive species which complex with the hydroxyl group of MePEG and provide an initiation site for the polymerization. The complex attacks the DL-lactide rings and the rings open up and are added to the chain, one-by-one, forming the polymer. The calculated molecular weight of the polymer is 3,333.

All reaction glassware was washed and rinsed with Sterile Water for Irrigation, USP, dried at 37° C., followed by depyrogenation at 250° C. for at least 1 hour. MePEG (240 g) and DL-lactide (160 g) were weighed and transferred to a round bottom glass flask using a stainless steel funnel. A 2 inch Teflon coated magnetic stir bar was added to the flask. The flask was sealed with a glass stopper and then immersed to the neck in a 140° C. oil bath. After the MePEG and DL-lactide melted, 2 ml of 95% stannous octoate (catalyst) was added to the flask. The flask was vigorously shaken immediately after the addition to ensure rapid mixing and then returned to the oil bath. The reaction was allowed to proceed for an additional 6 hours with heat and stirring. The liquid polymer was then poured into a stainless steel tray, covered and left in a chemical fume hood overnight (about 16 hours). The polymer solidified in the tray. The top of the tray was sealed using Parafilm®. The sealed tray containing the polymer was placed in a freezer at −20±5° C. for at least 0.5 hour. The polymer was then removed from the freezer, broken up into pieces and transferred to glass storage bottles and stored refrigerated at 2 to 8° C.

Preparation of a 50 mg/m² Dose

Preparation of the bulk and filling of paclitaxel/polymer matrix was accomplished essentially as follows. Reaction glassware was washed and rinsed with Sterile Water for Irrigation USP, and dried at 37° C., followed by depyrogenation at 250° C. for at least 1 hour. First, a phosphate buffer (0.08 M, pH 7.6) was prepared. The buffer was dispensed at the volume of 10 ml per vial. The vials were heated for 2 hours at 90° C. to dry the buffer. The temperature was then raised to 160° C. and the vials dried for an additional 3 hours.

The polymer was dissolved in acetonitrile at 15% w/v concentration with stirring and heat. The polymer solution was then centrifuged at 3000 rpm for 30 minutes. The supernatant was poured off and set aside. Additional acetonitrile was added to the precipitate and centrifuged a second time at 3000 rpm for 30 minutes. The second supernatant was pooled with the first supernatant. Paclitaxel was weighed and then added to the supernatant pool. The solution was brought to the final desired volume with acetonitrile.

The paclitaxel/polymer matrix solution is dispensed into the vials containing previously dried phosphate buffer at a volume of 10 ml per vial. The vials are then vacuum dried to remove the acetonitrile. The paclitaxel/polymer matrix is then terminally sterilized by irradiation with at least 2.5 Mrad Cobalt-60 (Co-60) x-rays.

Example 8

Manufacture of Microspheres

The equipment used for the manufacture of microspheres include: 200 ml water jacketed beaker (Kimax or Pyrex), Haake circulating water bath, overhead stirrer and controller with 2 inch diameter (4 blade, propeller type stainless steel stirrer—Fisher brand), 500 ml glass beaker, hot plate/stirrer (Corning brand), 4×50 ml polypropylene centrifuge tubes (Nalgene), glass scintillation vials with plastic insert caps, table top centrifuge (GPR Beckman), high speed centrifuge-floor model (JS 21 Beckman), Mettler analytical balance (AJ 100, 0.1 mg), Mettler digital top loading balance (AE 163, 0.01 mg), automatic pipetter (Gilson). Reagents include PCL (mol. wt. 10,000 to 20,000; Polysciences, Warrington Pa., USA), "washed" (see later method of "washing") EVA, PLA (mol. wt. 15,000 to 25,000; Polysciences), polyvinyl alcohol ("PVA"—mol. wt. 124,000 to 186,000; 99% hydrolyzed; Aldrich Chemical Co., Milwaukee Wis., USA), DCM or "methylene chloride"; HPLC grade Fisher scientific, and distilled water.

A. Preparation of 5% (w/v) Polymer Solutions

DCL (1.00 g) or PLA, or 0.50 g each of PLA and washed EVA was weighed directly into a 20 ml glass scintillation vial. Twenty milliliters of DCM was then added. The vial was capped and stored at room temperature (25° C. ) for one hour (occasional shaking may be used), or until all the polymer was dissolved. The solution may be stored at room temperature for at least two weeks.

B. Preparation of 5% (w/v) Stock Solution of PVA

Twenty-five grams of PVA was weighed directly into a 600 ml glass beaker and 500 ml of distilled water was added, along with a 3 inch Teflon coated stir bar. The beaker was covered with glass to decrease evaporation losses, and placed into a 2000 ml glass beaker containing 300 ml of water. The PVA was stirred at 300 rpm at 85° C. (Corning hot plate/stirrer) for 2 hours or until fully dissolved. Dissolution of the PVA was determined by a visual check; the solution should be clear. The solution was then transferred to a glass screw top storage container and stored at 4° C. for a maximum of two months. The solution, however must be warmed to room temperature before use or dilution.

C. Procedure for Producing Microspheres

Based on the size of microspheres being made (see Table 1), 100 ml of the PVA solution (concentrations given in Table 1) was placed into the 200 ml water jacketed beaker. Haake circulating water bath was connected to this beaker and the contents were allowed to equilibrate at 27° C. (+/−1° C.) for 10 minutes. Based on the size of microspheres being made (see Table 1), the start speed of the overhead stirrer was set, and the blade of the overhead stirrer placed half way down in the PVA solution. The stirrer was then started, and 10 ml of polymer solution (polymer solution used based on type of microspheres being produced) was then dripped into the stirring PVA over a period of 2 minutes using a 5 ml automatic pipetter. After 3 minutes the stir speed was adjusted (see Table 1), and the solution stirred for an additional 2.5 hours. The stirring blade was then removed from the microsphere preparation, and rinsed with 10 ml of distilled water so that the rinse solution drained into the microsphere preparation. The microsphere preparation was then poured into a 500 ml beaker, and the jacketed water bath washed with 70 ml of distilled water, which was also allowed to drain into the microsphere preparation. The 180 ml microsphere preparation was then stirred with a glass rod, and equal amounts were poured into four polypropylene 50 ml centrifuge tubes. The tubes were then capped, and centrifuged for 10 minutes (force given in Table 1). Forty-five milliliters of the PVA solution was drawn off of each microsphere pellet.

TABLE 1

PVA concentrations, stir speeds, and centrifugal force requirements for each diameter range of microspheres.

| PRODUCTION STAGE | MICROSPHERE DIAMETER RANGES | | |
|---|---|---|---|
| | 30 μm to 100 μm | 10 μm to 30 μm | 0.1 μm to 3 μm |
| PVA concentration | 2.5% (w/v) (i.e.,) dilute 5% stock with distilled water | 5% (w/v) (i.e., undiluted stock) | 3.5% (w/v) (i.e., dilute 5% stock with distilled water |
| Starting Stir Speed | 500 rpm +/− 50 rpm | 500 rpm +/− 50 rpm | 3000 rpm +/− 200 rpm |
| Adjusted Stir Speed | 500 rpm +/− 50 rpm | 500 rpm +/− 50 rpm | 2500 rpm +/− 200 rpm |
| Centrifuge Force | 1000 g +/− 100 g (Table top model) | 1000 g +/− 100 g (Table top model) | 10 000 g +/− 1000 g (High speed model) |

Five milliliters of distilled water was then added to each centrifuge tube and vortexed to resuspend the microspheres. The four microsphere suspensions were then pooled into one centrifuge tube along with 20 ml of distilled water, and centrifuged for another 10 minutes (force given in Table 1). This process was repeated two additional times for a total of three washes. The microspheres were then centrifuged a final time, and resuspended in 10 ml of distilled water. After the final wash, the microsphere preparation was transferred into a preweighed glass scintillation vial. The vial was capped, and left overnight at room temperature (25° C.) in order to allow the microspheres to sediment out under gravity. Since microspheres which fall in the size range of 0.1 um to 3 um do not sediment out under gravity, they were left in the 10 ml suspension.

D. Drying of 10 μm to 30 μm or 30 μm to 100 μm Diameter Microspheres

After the microspheres sat at room temperature overnight, the supernatant was drawn off of the sedimented microspheres. The microspheres were allowed to dry in the uncapped vial in a drawer for a period of one week or until they were fully dry (vial at constant weight). Faster drying may be accomplished by leaving the uncapped vial under a slow stream of nitrogen gas (flow approx. 10 ml/minute.) in the fume hood. When fully dry (vial at constant weight), the vial was weighed and capped. The labeled, capped vial was stored at room temperature in a drawer. Microspheres were normally stored no longer than 3 months.

E. Determining the Concentration of 0.1 μm to 3 μm Diameter Microsphere Suspension This size range of microspheres did not sediment out, so they were left in suspension at 4° C. for a maximum of four weeks. To determine the concentration of microspheres in the 10 ml suspension, a 200 μl sample of the suspension was pipetted into a 1.5 ml preweighed microfuge tube. The tube was then centrifuged at 10,000 g (Eppendorf table top microfuge), the supernatant removed, and the tube allowed to dry at 50° C. overnight. The tube was then reweighed in order to determine the weight of dried microspheres within the tube.

F. Manufacture of Paclitaxel Loaded Microsphere

In order to prepare paclitaxel containing microspheres, an appropriate amount of weighed paclitaxel (based upon the percentage of paclitaxel to be encapsulated) was placed directly into a 20 ml glass scintillation vial. Ten milliliters of an appropriate polymer solution was then added to the vial containing the paclitaxel, which was then vortexed until the paclitaxel dissolved.

Microspheres containing paclitaxel may then be produced essentially as described above in steps (C) through (E).

Example 9

Manufacure of Paclitaxal-loaded Star-shaped Poly (Lactic Acid) (PLA) and Poly(Lactide-co-Glycolic Acid) (PLGA) (PEG) Microspheres Microspheres containing 5, 10 or 20% paclitaxel in low molecular weight star-shaped PLA and PLGA (M.W.≈10, 000 by Gel Permeation Chromatography) were prepared by an oil-in-water emulsification technique. Briefly, the appropriate weights of the paclitaxel and 0.5 polymer were dissolved in 10 ml of dichloromethane and emulsified with a overhead propeller stirrer at the level of 3 (Fisher Scientific) into 100 ml 1% polyvinyl alcohol solution for about 3 hours. The formed microspheres were sieved and dried under vacuum at a temperature below 10° C. Yield of microspheres in the desired size range (53–90 μm) was about 50% and the encapsulation efficiency of paclitaxel in microspheres was about 98%.

Release studies were done by placing 2.5 mg of said microspheres in a 15 ml Teflon capped tube (with 10 ml phosphate buffer saline with albumin). Sampling daily (three sampling at the first day) to maintain the sink condition. Release study data showed that paclitaxel was released from the star-shaped microspheres 3 to 10 times faster than the conventional linear PLA and PLGA microspheres.

Example 10

Intrapericardical Micellar Paclitaxel Administration in a Porcine Model

Figure 1A:
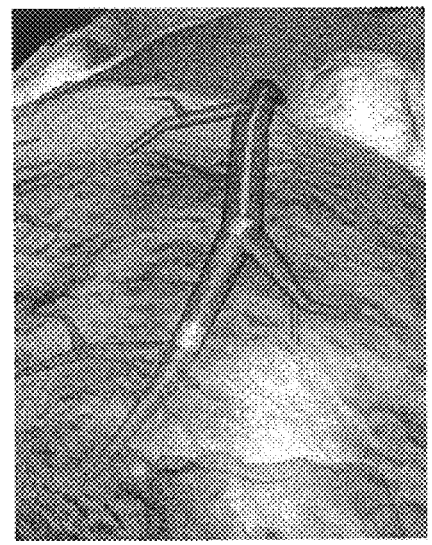
Figure 2:
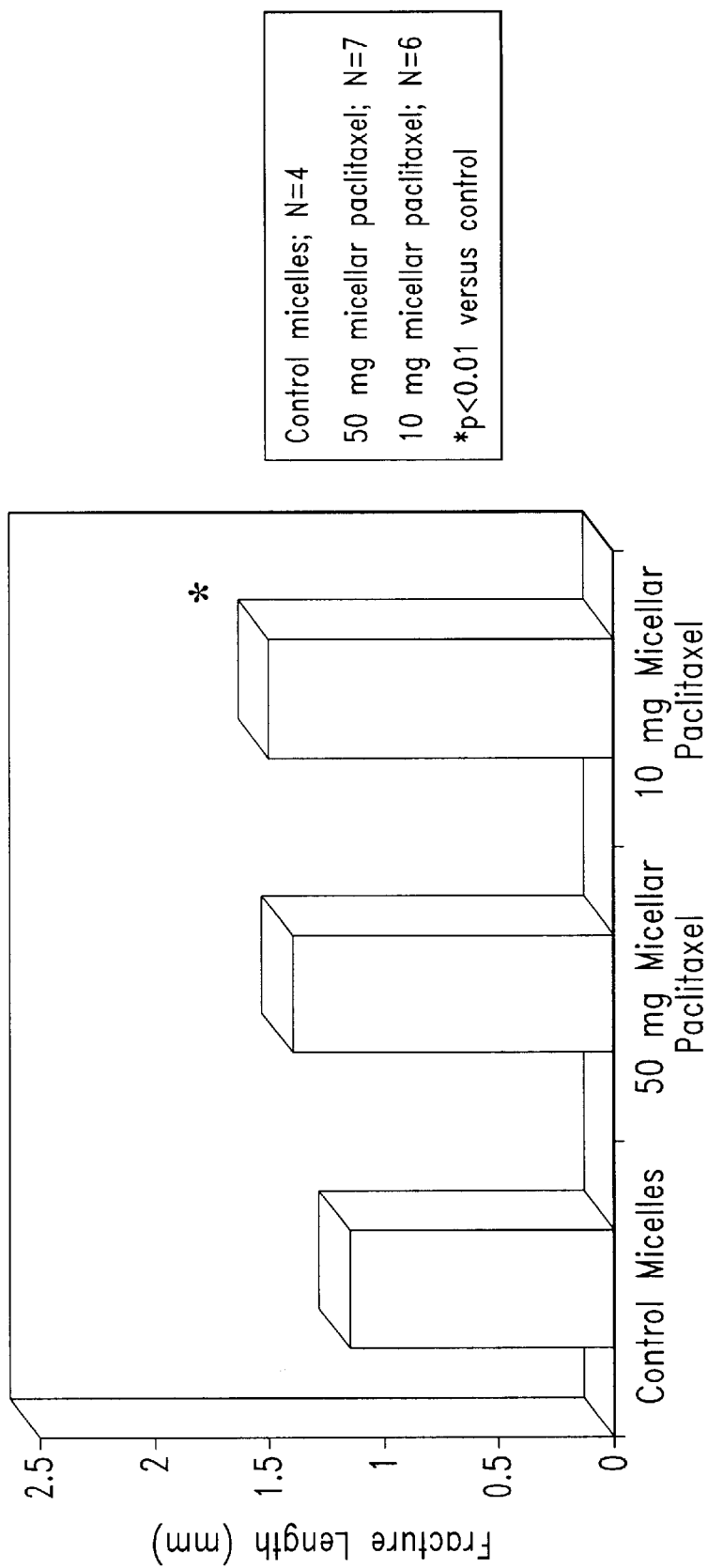
FIG. 2 is a bar graph which shows fracture length 28 days following balloon injury.
Figure 3:
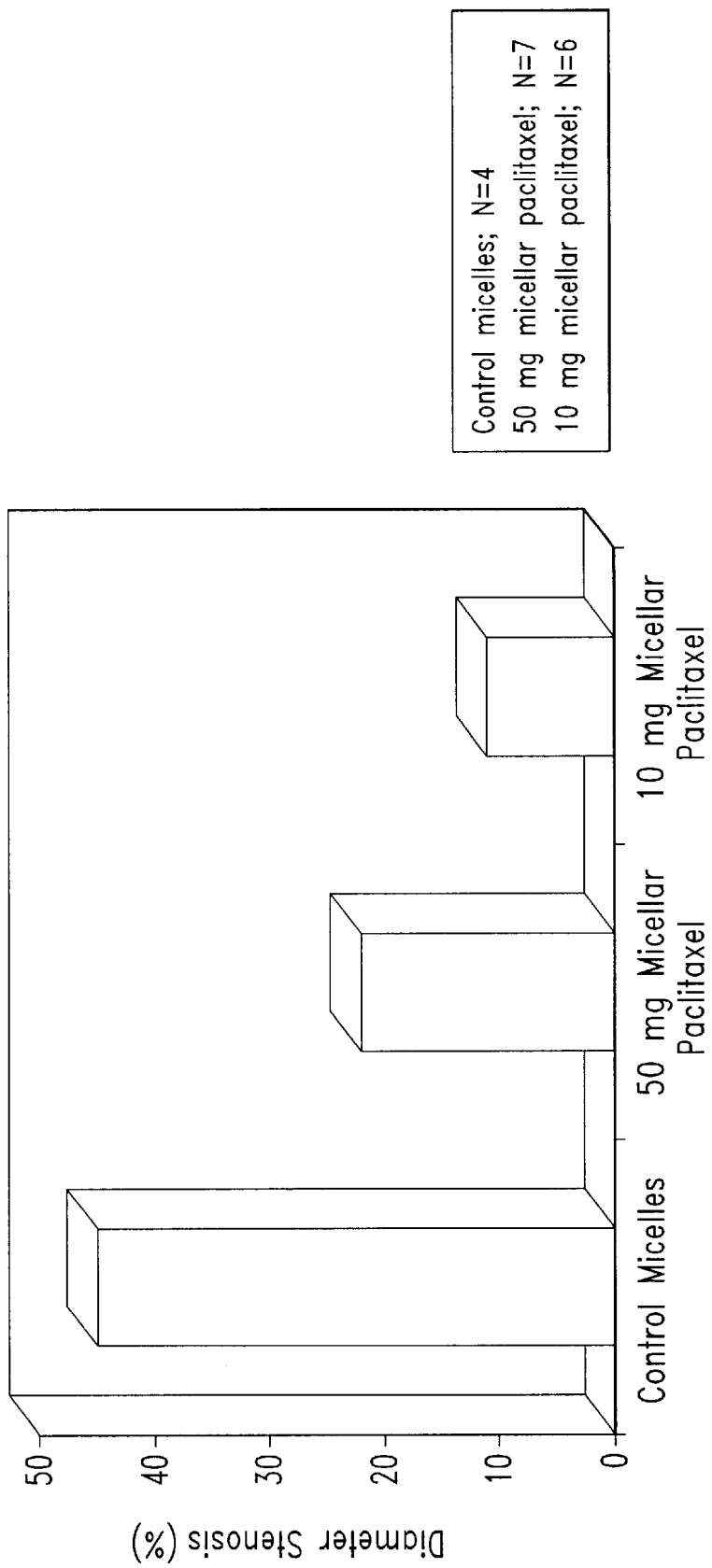
FIG. 3 is a bar graph which shows the percentage change in diameter following balloon injury and treatment with control micelles, or, 50 mg or 10 mg paclitaxel-loaded micelles.
Figure 4:
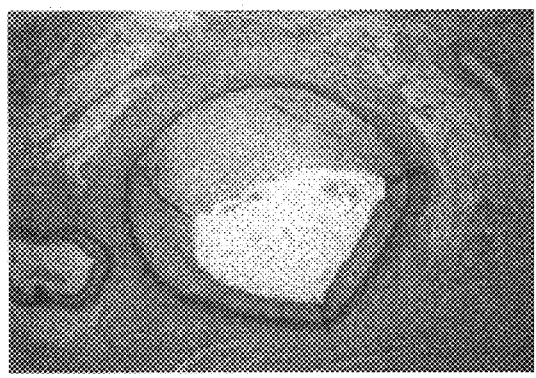
FIGS. 4 and 4A are photographs that depict swine coronary arteries following balloon injury and treatment with control micelles, or, 50 mg paclitaxel loaded micelles.
Figure 4A:
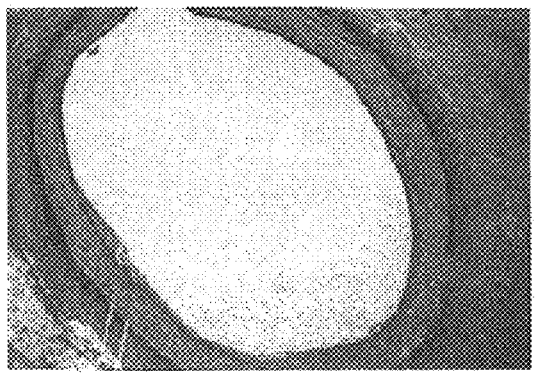
Figure 5:
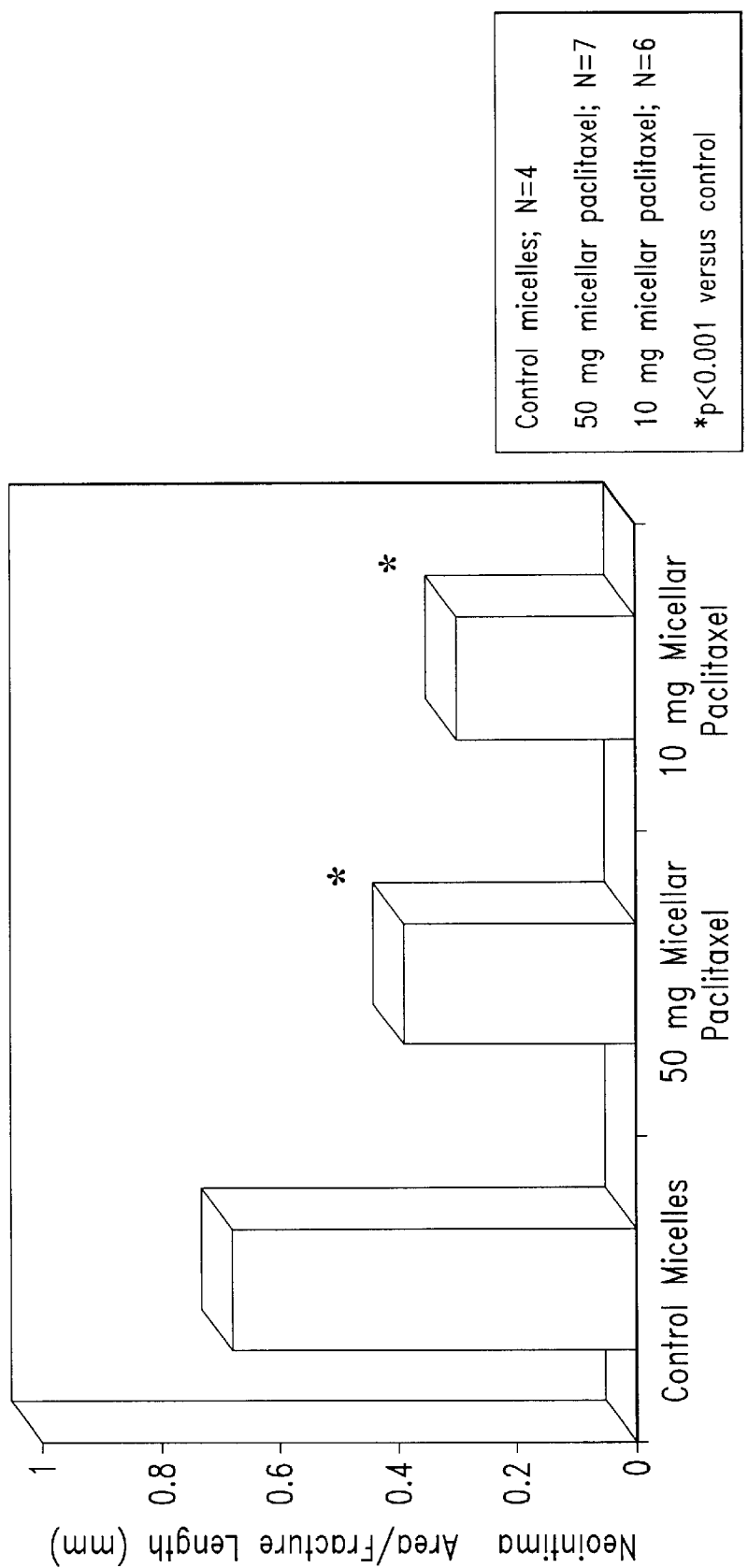
FIG. 5 is a bar graph which shows neoinimal area/fracture length.
Figure 6:
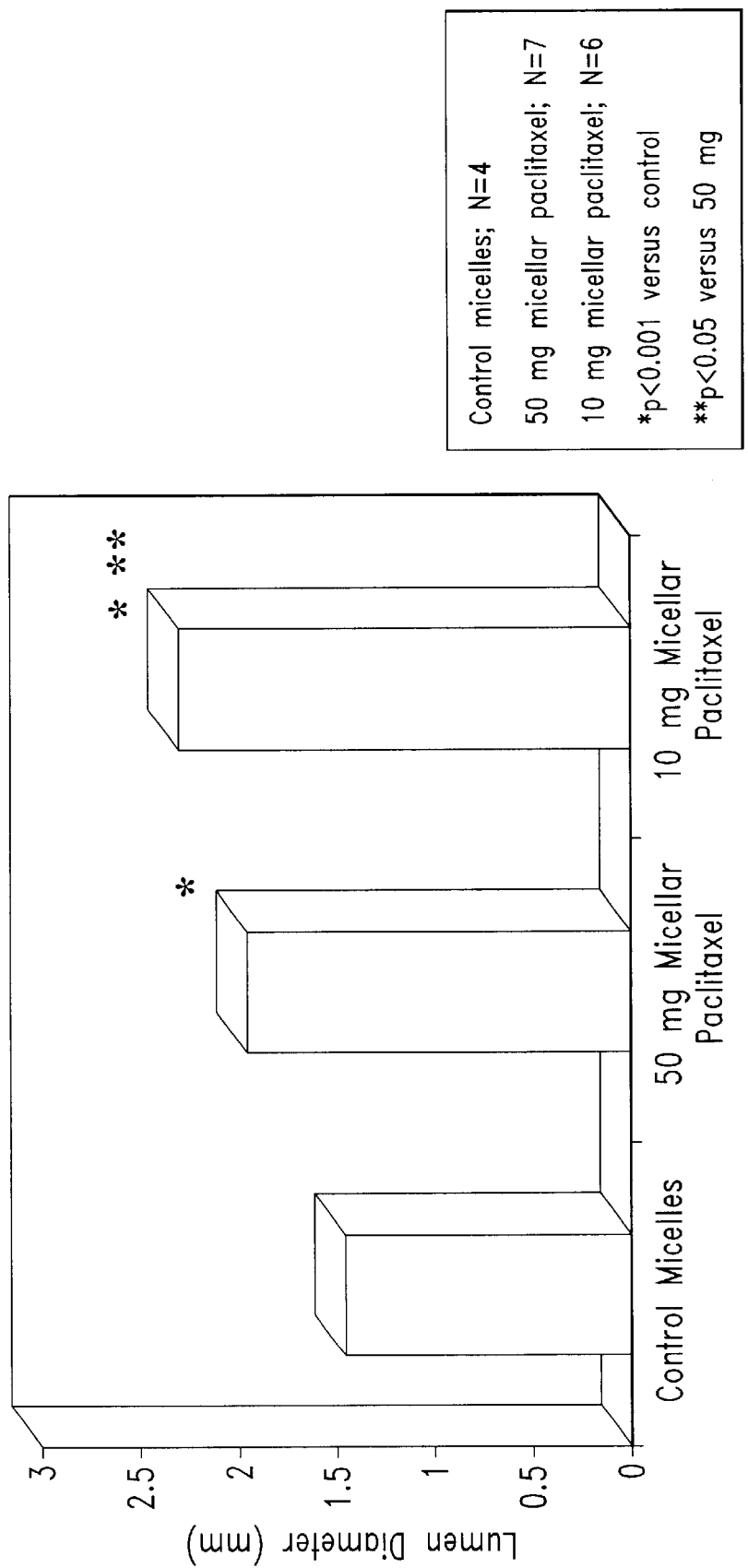
FIG. 6 is a bar graph which shows the lumen diameter following balloon injury and treatment with control micelles, or, 50 mg or 10 mg paclitaxel-loaded micelles.
Figure 7:
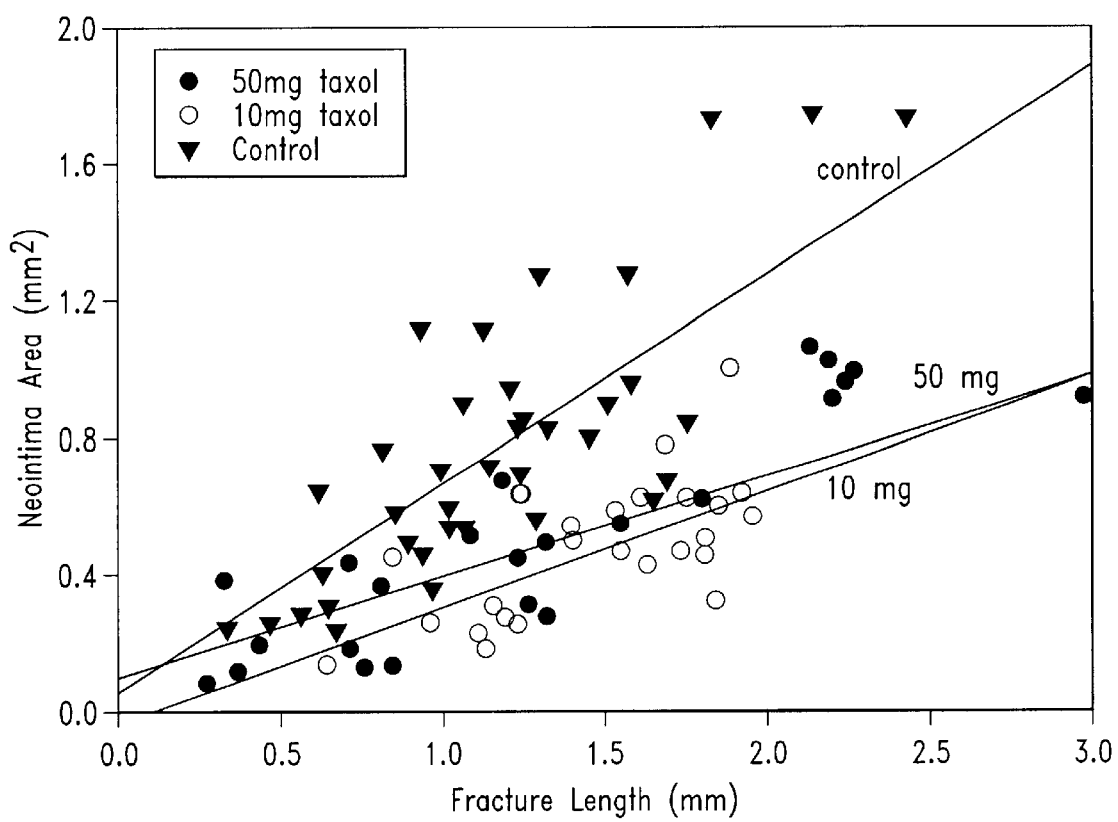
FIGS. 7–10B show further effects of the anti-microtubule agent on neointima structure.
Figure 8A:
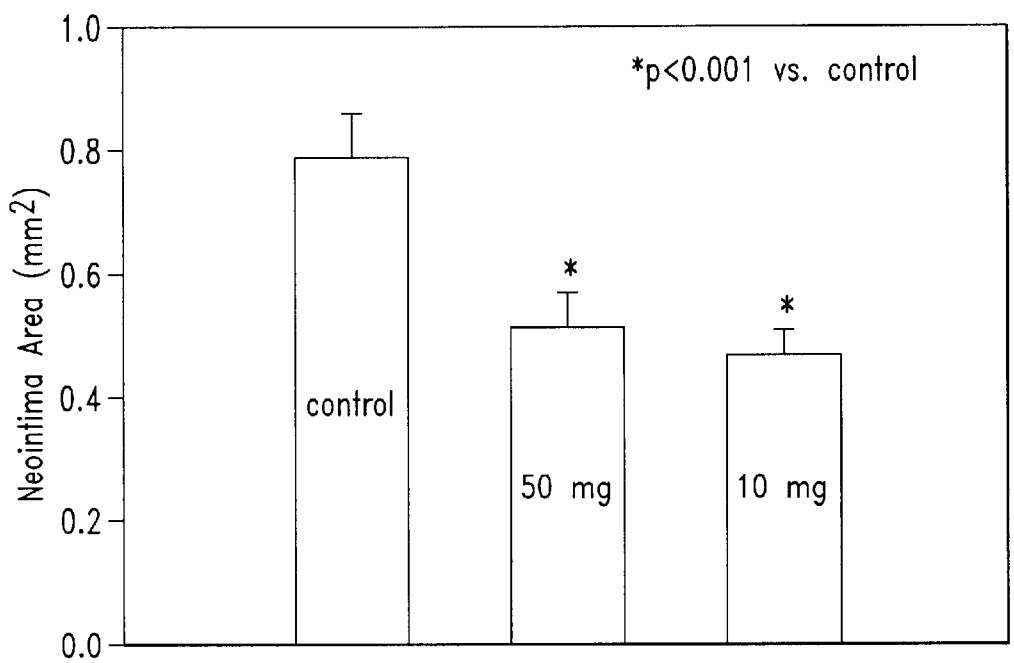
Figure 8B:
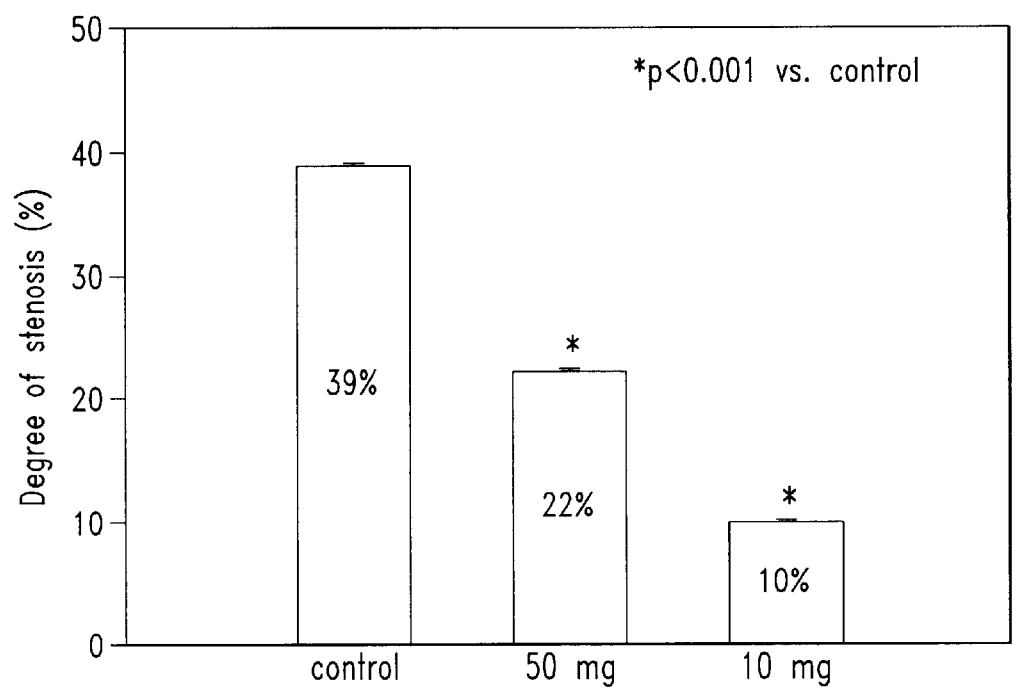
Figure 9A:
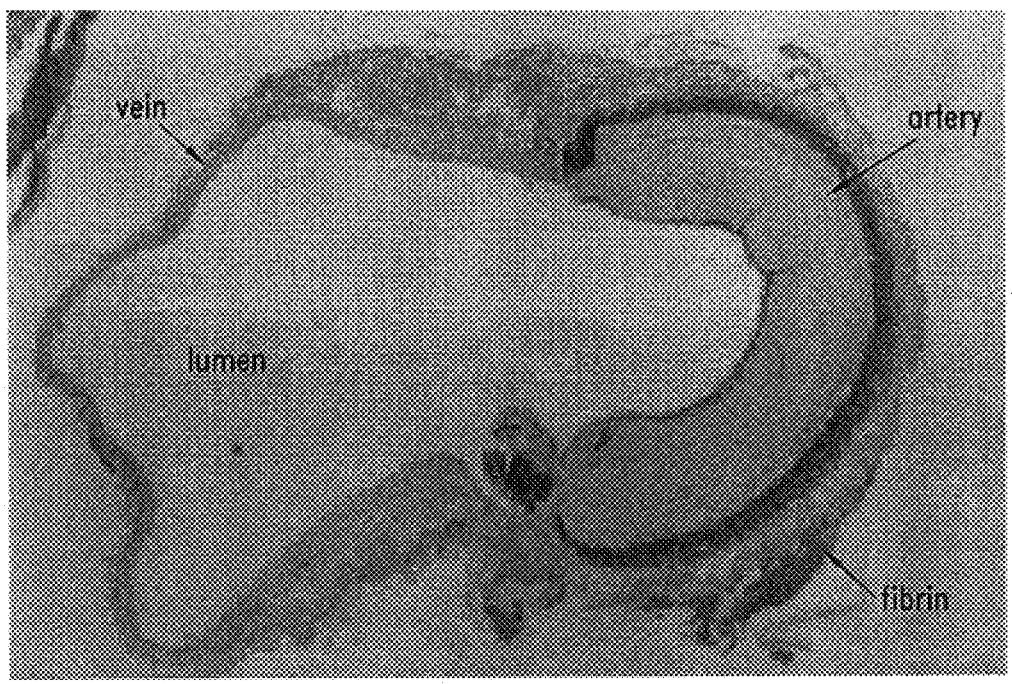
Figure 9B:
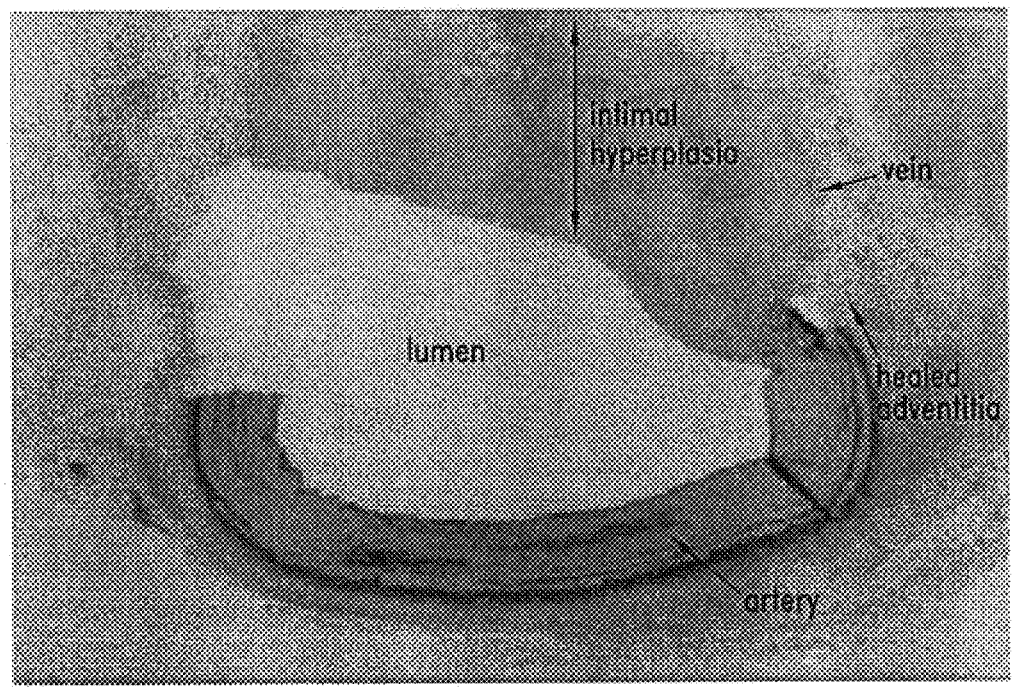
Figure 10A:
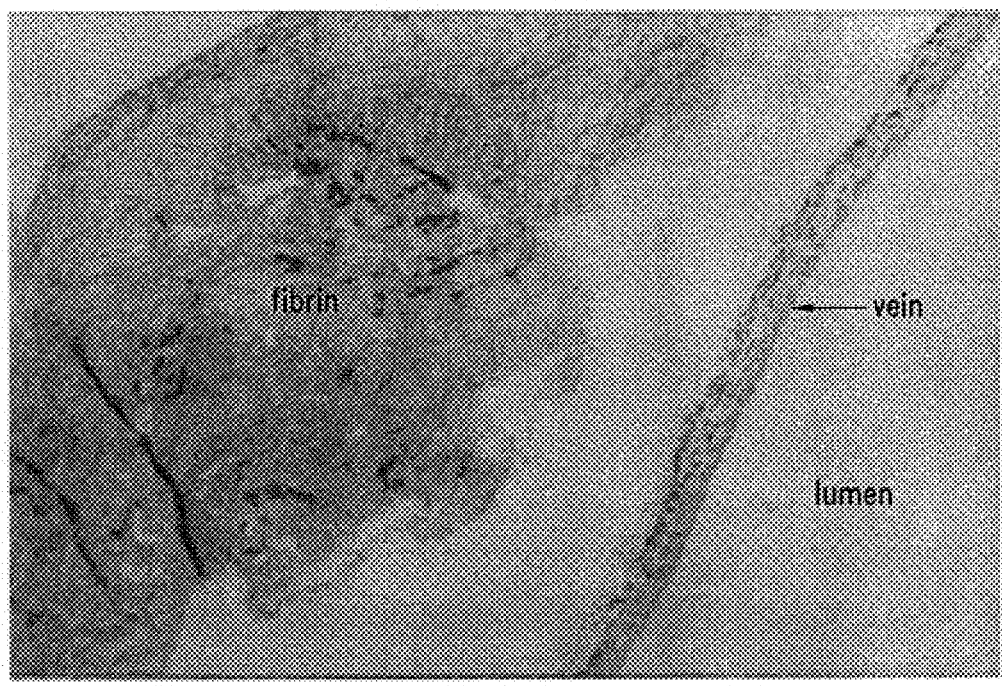
Figure 10B:
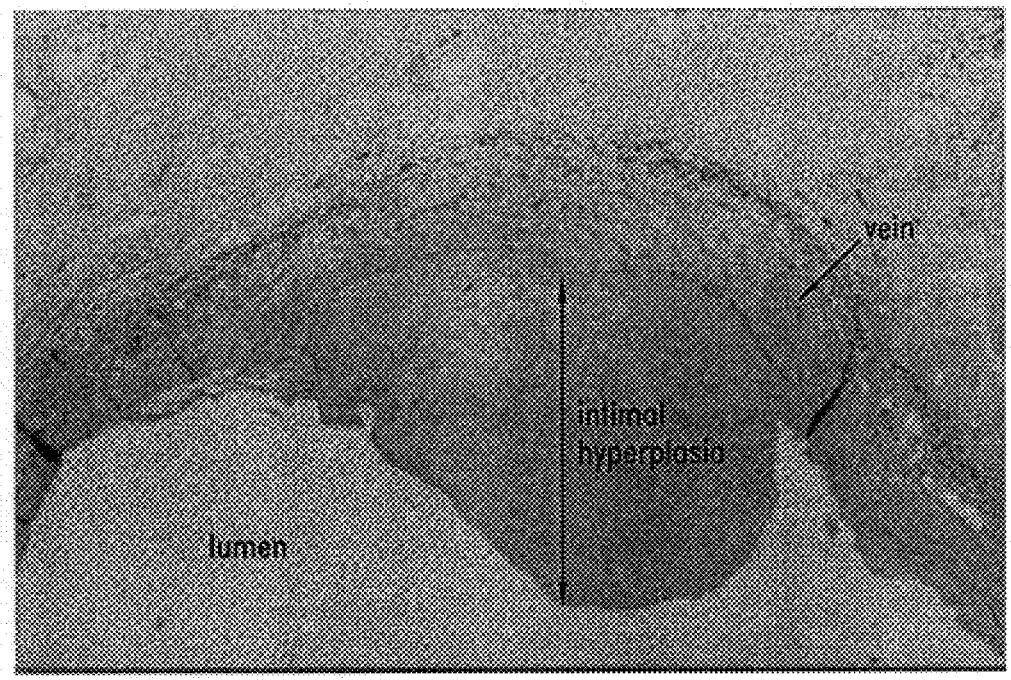

Juvenile farm pigs of approximately 20 kg weight receive angiography to permit arterial measurement. Balloon injury is then performed alternatively in the LAD or LC at an overstretch ratio of 1.3 to 1 (see FIGS. 1 and 1A). The alternative vessel receives a stent injury at the same overstretch ratio. Pericardial access and installation is obtained utilizing PerDUCER devices by Comedicus, Inc. (Minneapolis, Minn.).

The swine each receive a single infusion of unloaded micelles (control), or, 10 mg or 50 mg paclitaxel loaded micelles. Results are shown in FIGS. 2 through 6.

Example 11

Testing of Polymer Biocompatibilty when Delivered into the Pericardial Chamber of Rabbits The objective of this study was to examine the biocompatibility of a number of controlled drug release polymers for the treatment of blood vessel disease when released into the intrapericardial cavity (the cavity between the membrane surrounding the heart and the heart.

Briefly, rabbits were anesthesized and maintained on a respirator with halothane. Following standard surgical procedures to expose the chest cavity, the pericardial sac was identified and punctured with the needle and approximately 1 mL of the polymer in saline was injected. The layers of muscle and skin were then sutured and animals recovered. At the two-week timepoint, animals were euthanized, and the chest cavity opened. Tissues (pericardial membrane, and heart) were examined for adhesion formation and inflammation including erythema, fluid, necrosis, and thickening of the pericardial membrane. Tissues including the heart and pericardial membrane were prepared for histological analysis.

Three groups of rabbits were tested. These included saline (N=4), a hyaluronic acid formulation (N=4) and a Polylactic acid microsphere formulation (N=2). The four rabbits injected (1ml) with saline and the 4 animals injected (1 ml) with hyaluronic acid paste (20mg/ml and 40mg/ml) did not show any sign of toxicity at necropsy. A small area (1×1cm) of white soft material was present on the left ventricle close to the site of injection in the animals injected with microspheres (4mg/ml). The pericardium did not adhere to this tissue. The amount of fat surrounding the heart was remarkable in all animals and prevented thorough inspection of the pericardium at necropsy. Histology of the pericardial tissue following application of these formulations was conducted and did not show evidence of a chronic inflammatory reaction from the polymers.

These results demonstrate that the hyaluronic acid formulation and PLA microspheres are suitable polymers for intrapericardial delivery of drugs.

From the foregoing, it will be appreciated that, although specific embodiments of the invention have been described herein for purposes of illustration, various modifications may be made without deviating from the spirit and scope of the invention. Accordingly, the invention is not limited by the specific examples provided herein.

What is claimed is:

1. A method for treating or preventing disease of the pericardium, heart, or coronary vasculature, comprising administering intrapericardially to a patient an antimicrotubule agent, such that said disease of the pericardium, heart, or coronary vasculature is treated or prevented.

2. The method according to claim 1 wherein said antimicrotubule agent is paclitaxel, or an analogue or derivative thereof.

3. The method according to claim 1 wherein said disease is intimal hyperplasia.

4. The method according to claim 1 wherein said antimicrotubule agent further comprises a polymer.

5. The method according to claim 4 wherein said polymer is poly-lactic acid.

6. The method according to claim 4 wherein said polymer is hyaluronic acid.

* * * * *